(12) United States Patent
Podoleanu

(10) Patent No.: US 9,167,144 B2
(45) Date of Patent: Oct. 20, 2015

(54) CAMERA ADAPTER BASED OPTICAL IMAGING APPARATUS

(71) Applicant: UNIVERSITY OF KENT, Kent (GB)

(72) Inventor: Adrian Podoleanu, Kent (GB)

(73) Assignee: University of Kent (GB)

( * ) Notice: Subject to any disclaimer, the term of this patent is extended or adjusted under 35 U.S.C. 154(b) by 14 days.

(21) Appl. No.: 14/102,148

(22) Filed: Dec. 10, 2013

(65) Prior Publication Data

US 2014/0176693 A1    Jun. 26, 2014

Related U.S. Application Data

(63) Continuation of application No. 12/866,304, filed on Sep. 21, 2010, now Pat. No. 8,619,184.

(30) Foreign Application Priority Data

Feb. 8, 2008    (GB) .................................. 0802290.7

(51) Int. Cl.
  *H04N 5/232*    (2006.01)
  *A61B 3/10*     (2006.01)
  *G02B 21/00*    (2006.01)
  *G01B 9/02*     (2006.01)
  *A61B 3/14*     (2006.01)
  (Continued)

(52) U.S. Cl.
  CPC ................ *H04N 5/232* (2013.01); *A61B 3/102* (2013.01); *A61B 3/14* (2013.01); *G01B 9/0203* (2013.01); *G01B 9/02007* (2013.01); *G01B 9/02049* (2013.01); *G01B 9/02069* (2013.01); *G01B 9/02079* (2013.01); *G01B 9/02091* (2013.01); *G02B 21/0056* (2013.01);
  (Continued)

(58) Field of Classification Search
  CPC ..... H04N 5/2354; H04N 5/2251; A61B 3/113
  USPC ........................... 348/78, 370, 373, 375, 340
  See application file for complete search history.

(56) References Cited

U.S. PATENT DOCUMENTS 3,915,564 A * 10/1975 Urban .......................... 351/206
6,769,769 B2 * 8/2004 Podoleanu et al. ........... 351/221
(Continued)

FOREIGN PATENT DOCUMENTS

GB     2407155      4/2005
WO   WO 03/094706   11/2003

OTHER PUBLICATIONS

Podoleanu et al., "OCT En-face Images from the Retina with Adjustable Depth Resolution in Real Time," (Aug. 1999).
(Continued)

*Primary Examiner* — James Hannett
(74) *Attorney, Agent, or Firm* — Barnes & Thornburg LLP

(57) ABSTRACT

The invention describes several embodiments of an adapter which can make use of the devices in any commercially available digital cameras to transform the digital camera into a fundus camera for inspecting the back of the eye, or into a microscope. The camera adapter is adapted to be placed between the camera device and the object. The devices in the camera being used are at least its optical source, photodetector sensor, memory, shutter and autofocus. Means in the adapter are provided to employ these devices and allow camera to operate its autofocus capability and its different color sensors. Methods of investigation of an object are also presented of using the adapter to transform the camera into an imaging instrument, where the effect of adjustments of elements inside the adapter are guided by the displaying screen of the camera.

17 Claims, 9 Drawing Sheets

(51) Int. Cl.
*H04N 5/225* (2006.01)
*H04N 5/33* (2006.01)

(52) U.S. Cl.
CPC ......... *G02B 21/0064* (2013.01); *H04N 5/2252* (2013.01); *H04N 5/33* (2013.01); *G01B 2290/35* (2013.01); *G01B 2290/70* (2013.01)

(56) References Cited

U.S. PATENT DOCUMENTS

| 2001/0052935 | A1 | 12/2001 | Yano | |
| 2007/0041722 | A1 | 2/2007 | Fong | |
| 2007/0110416 | A1* | 5/2007 | Yamaguchi et al. | 396/27 |
| 2007/0291277 | A1* | 12/2007 | Everett et al. | 356/497 |
| 2010/0208201 | A1* | 8/2010 | Knighton et al. | 351/206 |
| 2013/0300919 | A1* | 11/2013 | Fletcher et al. | 348/360 |

OTHER PUBLICATIONS

Podoleanu, "Progress in the en-face optical coherence tomography applied to eye imaging," *Proc. of SPIE*, 6606: 66061-66069 (2007).

Podoleanu, "Simultaneous OCT/confocal-OCT/ICG system for imaging the eye," *Proc. of SPIE*, 5578: 159-166 (2004).

* cited by examiner

CAMERA ADAPTER BASED OPTICAL IMAGING APPARATUS

RELATED APPLICATION

This application is a continuation of corresponding U.S. patent application Ser. No. 12/866,304, filed Sep. 21, 2010, now U.S. Pat. No. 8,619,184.

FIELD OF THE INVENTION

This invention relates to a method and apparatus for imaging transparent objects in general and tissue in particular using digital cameras. The invention describes several adapters which can make use of the devices in commercial digital cameras to accomplish different functions, such as a fundus camera, or as an en-face optical coherence tomography (OCT) or as a channeled spectrum (Fourier domain) optical coherence tomography (CS-OCT), or as a non-invasive dual channel optical imaging instrument which can be used to provide simultaneous cross section OCT images and compound en-face images. In microscopy, the system delivers simultaneously cross sections from specimens and en-face oriented confocal microscopy (CM) images. If used for imaging the retina of the eye, then the system delivers simultaneously two images, OCT cross sections from the retina and en-face oriented fundus images, of the type delivered by a scanning laser ophthalmoscope (SLO) or a confocal SLO, i.e. the system can deliver OCT/SLO or OCT/CM dual images, depending on the application.

PRIOR ART AND BACKGROUND OF THE INVENTION

A variety of instruments which produce depth resolved information and imaging of the eye, tissue or industrial objects are known. They involve CM and OCT principles. A general problem with all these configurations is their large volume and high cost. This restricts their use to a few medical practices and research centres.

In the description which follows, reference is made primarily to the human eye and skin, however the invention is also applicable to measurements and imaging of any other objects which are sufficiently transparent for visible or infrared light, as well as for profilometry of any object which reflects visible or infrared light. In terms of imaging moving objects, reference is made primarily to two examples, live embryos or the retina of an eye. This has to be understood as merely a way to help the description and not as a restriction of the application of the present invention. As such, where the term "embryo" or "eye" or "retina" is used, a more general transparent and scattering object or organ may be sought instead, the invention could equally be applied to skin, heart, vessels, dental tissue, dental prostheses, paintings, powders and other scattering semi-transparent objects, moving or non-moving. The dual imaging aspect of the invention is especially useful for moving objects.

All known imaging systems for the eye, such as fundus cameras, slit cameras, SLO and OCT systems as well as imaging systems for skin, other tissue, profilometry use an optical source, scanners, some optics and a reader, in the form of photodetector devices or 1D or 2D photodetector arrays.

However, all these systems are inaccessible to most of the small medical practices and small businesses due to their high cost. Some use sophisticated optical sources, such as femtosecond lasers pulsed or CW lasers, specialized sources such as superluminiscent diodes (SLD). These optical imaging systems also use specialized 1D and 2D photodetector arrays, or many pixels, high dynamic CCD or CMOS cameras, of high cost.

The implementation of such systems on specialized chin rests for imaging the eye or microscopy on highly specialised frames lead to a further increase in their price.

There are instances when home, cross section or en-face images would be needed of translucent objects, such as nails, sheets of paper, objects of ceramics or porcelain, etc. A 1D profile of reflectivity in the anterior chamber of the eye could be used to evaluate the sugar content eliminating the need of the current invasive measurement methods using a drop of blood. The bulky format of available OCT systems and their cost prevent OCT technology from replacing invasive methods, or penetrating the consumer market, to the level and extent of electrical appliances. High skills are required to operate such OCT systems, at the level of a well educated Physicist, engineer or medical practitioner. They are sophisticated and complex and cannot be handled in the way a PC or an electrical appliance is used by any consumer.

Due to the reasons mentioned above, it is hard to imagine that such sophisticated imaging systems would have a wide spread in the countryside and small towns where authorities struggle in ensuring provision of even basic medical devices. Also, small companies cannot afford to purchase such systems for profilometry or topography, distance measurement, or correlation measurements due to their high cost.

In the battle field, ophthalmologists need OCT systems to evaluate eye damage. Art conservationist need OCT systems in harsh environments, in either very hot conditions or very cold. Underwater inspection of relics by conservationists or salvage teams is another example where portable and compact high resolution instruments are needed. The bulky systems known today cannot be easily made transportable or adapted for harsh conditions.

Therefore, a need exists for more compact high depth resolution measurement and imaging systems, portable and of much lower cost to allow the spread of confocal microscopy technology and of OCT technology to satisfy the needs of ordinary people without resorting to specialized equipment or advice, or to satisfy the needs of specialists working in harsh weather conditions or difficult environment and to be used by small practices in diagnostic as well as by small companies in industry.

There are also known imaging and measurement instruments using monochrome high performance cameras. The imaging of moving organs or objects or fast evolving phenomena is often difficult due to the time required to collect repetitive data for different values of polarisation, wavelength or angular incidence for polarisation, spectroscopic and speckle reduction imaging respectively.

Therefore a need exists to speed up the acquisition by conveniently and advantageously employing the novel features available in modern digital cameras.

A form of spectral domain OCT, called channeled spectrum (CS) of Fourier domain OCT is based on reading the channeled spectrum at the output of an interferometer using a spectrometer, as described in "Displacement Sensor Using Channeled Spectrum Dispersed on a Linear CCD Array", by S. Taplin, A. Gh. Podoleanu, D. J. Webb, D. A. Jackson, published in Electron. Lett. 29, No. 10, (1993), pp. 896-897 and in "Channeled Spectrum Liquid Refractometer", by A. Gh. Podoleanu S. Taplin, D. J. Webb, D. A. Jackson, published in Rev. Sci. Instr., vol. 64, No. 10, pp. 3028-9, (1993). By adding a transversal scanning head to the configuration described in these two papers, OCT functionality is achieved. However, such methods produce B-scan OCT images only. It will be desirable to have an en-face image to guide the B-scan acquisition of moving embryos, organs or any other moving samples. It will also be useful to see the eye fundus when cross-sectioning the retina. Fourier domain optical coherence tomography systems are based on an interferometer whose spectrum is read by a linear CCD array. Increase in the speed and dynamic range of digital linear cameras allowed progress in this field. Cameras with 2048 pixels which could be read at more than 100 kHz line rate are now available. SLR cameras with more than 1000×1000 pixels and with a 10 microsecond acquisition times are also available, which shows that the performance of commercially available cameras improved to the level of scientific more expensive cameras.

OCT has mainly evolved in the direction of producing cross-sectional images, most commonly perpendicular to the plane of images delivered by a microscope or by a SLO. The depth resolution in SLO is 30-100 µm coarser than that in OCT while the transversal resolution in OCT is affected by random interference effects from different scattering centers (speckle), inexistent in SLO images. Therefore, there is scope in combining SLO with OCT. Different avenues have been evaluated, to provide an SLO using CS-OCT systems. The main motivation for OCT/SLO combination is to provide orientation to the OCT channel. Crucial for the operation is pixel to pixel correspondence between the two channels, OCT and SLO, which can only be ensured if both channels share the same transverse scanner to scan the beam across the eye.

An equivalent SLO image can be generated from several OCT B-scans. Then, by software means, an SLO image can be inferred without using a beamsplitter or a separate confocal receiver. After a 3D data set acquisition, a confocal microscopy image of the embryo (or an SLO-like image of the retina is generated) and then the B-scan OCT images can be revisited through the 3D data set with simultaneous display of the synthesized CM (or SLO) image. SLO-like image cane be inferred from B-scans using CS-OCT systems, as reported in Hong, Y., Makita, S., Yamanari, M., Miura, M., Kim, S., Yatagai, T., Yasuno, Y 2007, "Three-dimensional visualization of choroidal vessels by using standard and ultra-high resolution scattering optical coherence angiography", published in Opt. Express 15, 7538-7550 or by Jiao, S I., Wu, C. Y., Knighton, R. W., Gregori, G., Puliafito, C. A., 2006, "Registration of high-density cross sectional images to the fundus image in spectral-domain ophthalmic optical coherence tomography", Published in Optics Express 14, 3368-3376.

The main advantage of the spectral OCT method relies on its high speed which allows collection of a large data set of pixels. With a high density of 65536 A-scans, obtained at 29 kHz, 2.25 s are required for the whole volume. The transversal resolution along the synthesis axis of the SLO image is given by the spatial sampling, i.e. by the lateral interval from a B-scan to the next B-scan along a rectangular direction to that contained in the B-scan image. Such SLO-like C-scan images exhibit the normal transversal resolution (15-20 µm) along the B-scan lateral coordinate (X) and the coarse sampling interval, along the lateral rectangular direction (Y). For instance, let us say that the image is from an area of 4 mm×4 mm on the retina of 512×128 pixels. This means that the Y-pixel size is 4 mm/128=31 µm. This size could be reduced by increasing the acquisition time in order to capture more B-scan images but would also result in more cumulated artefacts due to movement. If correction is made for the large transversal pixel size along the Y-axis, to achieve the normal pixel size of 15 µm in an aberrated eye, acquisition time would increase to over 4.5 s.

The disadvantage of this method is that the CM (or the en-face fundus image) is generated after (i) acquisition is complete and (ii) software evaluation, both steps requiring some time. As another disadvantage, as presented above, the transversal resolution along the sampling direction of B-scan repetition is coarser than the transversal resolution along the lateral direction in the FD-OCT image.

Other possibility is to produce an en-face cumulated image (microscopy or SLO) and then switch the system to acquire a fast B-scan OCT image. The operation can be sequential and not simultaneous because the reference beam has to be blocked when acquiring the CM (or SLO) image, otherwise the reference beam saturates the CM (SLO) channel or produces noise in this channel.

Another possibility is to divert light form the object towards a separate splitter, as disclosed in the U.S. Pat. No. 5,975,697 for a time domain OCT and for a CS-OCT system in US2008/0088852 A1 by J. Rogers and M. Hathaway. This method however reduces the amount of light used for generating the OCT images.

Therefore, the present invention seeks to overcome the above disadvantages, providing configurations and methods of operation, characterized by simultaneous parallel acquisition of the OCT information and of microscopy (eye fundus) information.

SUMMARY OF THE INVENTION

The present invention solves the above problems by means of methods and several configurations of apparatuses devised around commercially available CCD cameras.

In a particular aspect, there is provided an adapter as set out in claim 1 and a system as set out in claim 8.

In preferred embodiments, the methods and apparatuses make use of the elements which equip any commercial digital photo camera, a photodetector array, a flash optical source, a guiding beam for automatic focus, shutter button, diaphragm control, shutter time adjustment and interface optics which transfer the light from the object imaged to the photodetector array including the automatic focus, electronic interface to transfer the image or images stored in the photodetector array to a separate computing system and the memory card.

The present application describes methods and devices to produce images similar to those produced by sophisticated and dedicated fundus cameras or OCT systems when imaging the eye and methods and devices to produce images similar to those produced by sophisticated and dedicated microscopes or OCT systems when imaging skin, other types of tissue, industrial objects or profilometry instruments. The application therefore describes adapters to host conventional commercially available cameras and allow the elements above equipping any camera to be used conveniently to accomplish several operation functions. The adapters have to perform functions required by the optical principle involved as well as to adapt the existing elements to commercially available cameras to best accomplish functions to which they have not initially been designed for, while at the same time minimize the disadvantages of the original design which optimised the camera for its main function, photography. For instance, optical sources in photography are flash sources, they do not emit a continuous wave (CW) generally used in high resolution imaging. One the other hand, the IR beam, emits CW but has much lower power. Both sources, the flash and the IR beam are divergent. The flash may also be of different shapes and exhibit narrow spectral spikes. As another disadvantage, the photodetector array and the source are placed within the same compact spatial block and assembled to accomplish photography, a different function than that envisaged by the present application.

The present application presents devices and methods to take advantage of the specificity of elements designed for digital photography. For instance, the advancement in the timing of flashes towards shorter time bursts suits ideally the needs for OCT, where to avoid the washout of fringes, ms and sub-ms duration of fringe readout is required.

The present application also describes methods and devices to produce depth resolved information and images using colour cameras which can be extended to specialised systems for speed of operation and versatility.

The application will describe methods and devices to image different objects using principles of microscopy or fundus cameras, or OCT, methods and devices which can be implemented using the elements in any commercially available cameras, including the possibility of using external optical sources, normally associated with photography, such as powerful controllable flashes, USB or TTL.

In keeping with the invention, a much lower cost solution is provided which employs the elements in any commercially available camera to achieve different functionality. In order to make use of such elements, the present invention provides different versions of adapters which transform a camera (or suits several cameras to be transformed) into specialized imaging instruments.

Thus, in a first aspect the invention provides an adapter which transforms a conventional commercial camera into an en-face OCT imaging systems with demodulation based on known principles of Hilbert transformation or phase shifting interferometry. Two or three images have to be at least collected in order to obtain an en-face OCT image (a C-scan OCT image). These can be acquired for each press of the shutter. Alternatively, by using the rapid fire of several flashes, feature equipping modern cameras or separate flash optical sources, several phase steps are created and for each step an image is acquired with all steps triggered by pressing the shutter once only.

In a second aspect, the three colour sensitive parts of the sensor are used to provide the three phase shifts for one data acquisition step of an en-face OCT image (C-scan).

In a third aspect, the three colour sensitive parts of the photodetector sensor are used to provide a specific quantity OCT en-face imaging by producing an en-face OCT image for each spectral optical band as determined by the spectral sensitivity of the sensor and the spectral emission of the light source, where the specific quantity could be either wavelength for spectroscopic analysis, polarisation, angular incidence for speckle reduction or step delay for range extension and curvature of curved objects such as the cornea.

In a fourth aspect, the invention provides an adapter which transforms a conventional commercial camera into a longitudinal OCT system, where a depth profile, i.e. an A-scan can be obtained using CS-OCT. This could be used for thickness evaluation of thin translucent objects, such as the cornea and paper, to determine the length of the anterior chamber in eyes to sense variations in the glucose level in blood, could be used to trace scratches for forensic analysis, etc.

In a fifth aspect, the invention provides for an enhanced version of the above where the same line of pixels in a colour digital camera are used to provide simultaneously three A-scans for the three spectral bands of the three sensitive parts of the sensor.

In a sixth aspect, the invention provides for an adapter which uses the CS-OCT principle, where the light from a low coherence interferometer is dispersed or diffracted in a spectrometer type set-up and the result is launched to the sensor array in a camera to produce an A-scan reflectivity profile from the object to be measured, or by using line illumination, to generate a cross section image, i.e. a B-scan OCT image.

In a seventh aspect the invention discloses an adapter which uses the CS-OCT principle and a transversal scanner to generate either a cross section image, i.e. a B-scan OCT image (a lateral x depth map) or to collect volume data from a sample by repeating the acquisition of several B-scan OCT images.

In an eighth aspect, the present invention relates to an adapter which is based on channeled spectrum low coherence interferometer where in order to eliminate the mirror terms in CS-OCT, the reference beam in the interferometer is shifted laterally relatively in relation to the object beam before hitting the spectrometer.

In a ninth aspect, the present invention relates to an adapter which is based on channeled spectrum low coherence interferometer where in order to avoid saturation of a separate confocal receiver due to the reference beam, the reference beam in the interferometer is shifted laterally relatively in relation to the object beam before hitting the spectrometer. The dispersing element in the spectrometer may utilize diffraction or dispersion, i.e. it may employ a diffraction grating or a prism to angularly deflect the rays according to their wavelength or frequency. When a diffraction grating is used, the two interferometer beams, object and reference are slightly laterally shifted and the light in the zero order from the object beam is sent towards the CM (SLO) channel and the light in higher diffraction orders serves producing the A-scan OCT image by interference on the sensor array. When using a prism, reflection from one facet of the prism is used to divert light from the object beam towards a CM (SLO) receiver while the two beams, object and reference, are laterally shifted, then suffer dispersion and then interfere on the sensor array. The invention uses an optimised lateral shift of the two beams. The shift value is a minimum to ensure that no reference beam penetrates the CM (SLO) aperture in either case of the dispersing element mentioned above, diffraction grating or prism, and not too large to avoid the decrease in the spectrometer sensitivity due to the spectrometer resolution. In this way, simultaneous measurement of intensity of light using the confocal receiver with the A-scan OCT provided by the sensor array is made possible. The adapter may also include a device or devices for phase modulation or frequency shifting to provide means for full range CS-OCT, where the mirror terms are eliminated by constructing the complex Fourier transformation.

In this aspect, variations are admitted in the form of: (i) using a 2D transversal scanner to scan a flying spot over the object to be measured or imaged, with the confocal receiver employing a point photodetector and (ii) using a 1D transversal scanner to scan an illuminating line over the object, in which case the confocal receiver employs another 2D camera utilised as a line camera, or the confocal receiver uses a line camera, where in all cases such system provides simultaneously an en-face image (microscopy or eye fundus) with volume collection of multiple B-scans OCT images, In a tenth aspect, the invention provides an optical configuration with minimal losses where a 50/50 beamsplitter is used to create two shifted object and reference beams for two cameras which are assembled in the adapter to operate in CS-OCT regime.

The lateral shift of the two beams can be customised for two possible goals: (i) to eliminate the noise due to autocorrelation terms in each arm of the OCT interferometer, eliminate the zero frequency and the mirror terms which lead to ghost images for OPD values of the same modulus but opposite sign; (ii) by adding confocal receivers, where the two object beams, output of the beamsplitter are subject to no spectral analysis and are summed up in the confocal receivers, while the object and reference beams are spectrally analysed by each spectrometer and their results is subtracted, and where the lateral shift of the object and reference beams prior to the 50/50 beamsplitter is just sufficient to displace the reference beam out of the input apertures of the two confocal receivers. In this aspect, variations are admitted in the form of: (i) using a 2D transversal scanner to scan a flying spot over the object to be measured or imaged, with the two confocal receivers employing point photodetectors and (ii) using a 1D transversal scanner to scan an illuminating line over the object, in which case the confocal receivers use two other 2D cameras utilised as line cameras, or the confocal receivers use line cameras, where in either case such system provides simultaneously an en-face image (microscopy or eye fundus) with volume collection of multiple B-scans OCT images.

In an eleventh aspect, the invention provides for an adapter where the three colour sensitive parts of the photodetector sensor are used to provide a specific quantity longitudinal OCT imaging (A-scan or B-scan) by producing a longitudinal OCT image (A-scan or B-scan) for each spectral optical band as determined by the spectral sensitivity of the sensor and the spectral emission of the light source, where the specific quantity could be either wavelength for spectroscopic analysis, polarisation or angular incidence for speckle reduction.

In an twelve aspect of the present invention, there is provided an adapter which transforms a digital camera into a fundus camera.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which presently preferred embodiments of the invention will now be illustrated by way of example.

It is expressly understood, however, that the drawings are for the purpose of illustration and description only and are not intended as a definition of the limits of the invention. Other features of the present invention, as well as other objects and advantages attendant thereto, are set forth in the following description and the accompanying drawings in which like reference numerals depict like elements. Accordingly, various embodiments of the optical imaging apparatus of the present invention will now be described by reference to the following drawings wherein.

DETAILED DESCRIPTION OF THE PREFERRED EMBODIMENTS

Figure 1:
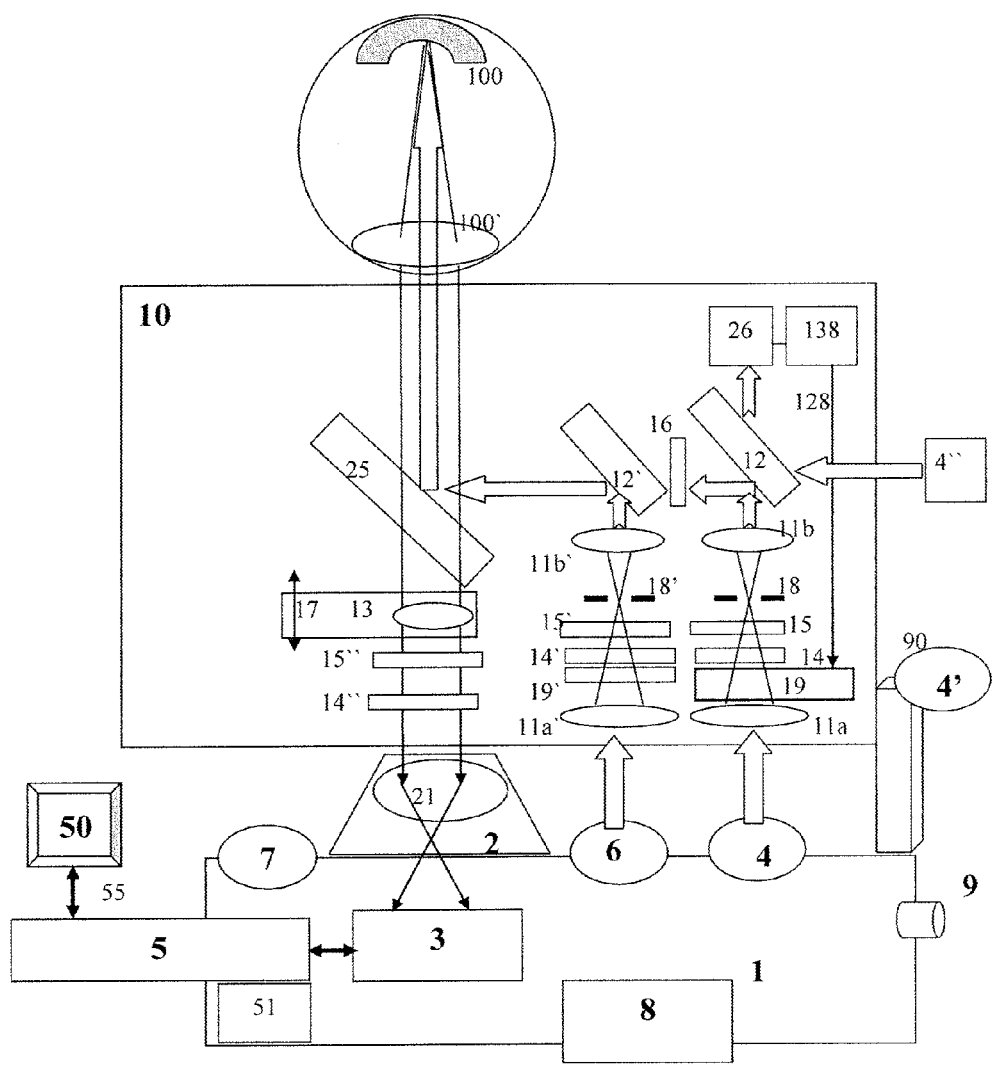
FIG. 1 shows a first embodiment of the present invention where a dedicated adapter uses a commercially available camera to collect eye fundus images.

Various features of the present invention, as well as other objects and advantages attendant thereto, are set forth in the following description and the accompanying drawings in which like reference numerals depict like elements.

1. FUNDUS CAMERA

A fundus camera for imaging the retina, as well as OCT imagers involve and make use of techniques known in the art, to produce images using CCD cameras or arrays of photodetectors. They use optical sources and special interfaces to image the retina and transfer the reflected light into a 2D pattern projected on the CCD array. By adding a reference beam to the beam conveying the 2D information carried by the object beam reflected from the target, a full field or a coherence radar OCT system is obtained. In order to adjust the position in depth where the image is collected from, the OCT systems have means for longitudinal scanning of the reference path length, have means for controlling the phase and polarization in order to maximize the interference signal and have means to display images. These systems generate C-scan images, i.e. constant depth images with thickness determined by the coherence length of the optical source employed. In a Cartesian coordinate system, where the x-y plane is the plane in which en-face images lie, and the z axis represents the depth direction, B-scans are longitudinal sections in planes such as x-z or y-z planes containing the z axis, and C-scans are transverse sections in planes parallel to the x-y plane.

By spectral decomposition of the light output from the interferometer, depth information is encoded in the modulation of the spectrum observed and a linear CCD camera can provide in this way, with no mechanical scanning, a reflectivity profile in depth, an A-scan. However these line cameras are expensive and the cost of camera Link cards and associated I/O boards adds to the high cost. The systems are also assembled on specialised chin rests or microscopes, are bulky and non-transportable.

Optical sources and photodetector arrays equip any commercially available digital photo cameras. As they are mass produced, their cost is much lower than those of optical sources and CCD cameras used in the known reports so far.

The present invention discloses different adapters which can transform a conventional commercial camera into a versatile, multi-functional high resolution single or dual channel measurement or imaging instrument.

As shown in FIG. 1, a commercially available camera, 1, has the following elements, an objective, 2, equipped with focusing optics, usually a group of lenses, 21, a 2D photodetector array, 3, an optical source, 4, usually a flash lamp, electronics interface block, 5, to handle the digital data equipped with a connector, usually a USB connector, to connect the camera to a PC and an infrared (IR) source for aiding the focus, 6. The camera is also equipped with a viewer, 7, to observe the object to be imaged, 100. This in FIG. 1 is the retina of an human or animal eye.

To acquire images from the object 100, an adapter, 10 is used according to the invention. The adapter contains an optical splitter, shown in the form of a plate beam-splitter, 25, in FIG. 1. Light from the object returns to the camera 1 via the splitter 25. To illuminate the object 100 in FIG. 1, using the flash lamp, 4, the adapter produces a collimated beam using focusing elements, 11a and 11b and a reflector, 12. Similarly, to convey the beam from the IR source 6, focusing elements 11a' and 11b' and a reflector 12' are used. This is required because usually, the flash lamps in cameras produce divergent beams. The focusing elements 11a and 11b and 11a' and 11b' produce collimated beams of 3-6 mm, preferably 3 mm to avoid the need of dilating the pupil. Spatial filtering is achieved with pinholes 18 and 18'.

Optical spectral filters 19 and 19' are placed in the beams of the flash source 4 and IR 6 to narrow their band to improve the accuracy of spectroscopic analysis. The adapter and digital camera and eventually another optical source, 4', are secured mechanically via a solid miniature support 90.

Light reflected by the optical splitter 25 passes through the eye pupil and anterior chamber, 100', towards the retina 100. An intermediate focusing element, 13, is required to fit the retina image on the 2D photodetector array 3. The elements 13 and the camera focusing element 21 are used jointly to produce a focused image of the retina on the 2D photodetector array 3, when is either illuminated by the flash lamp 4 or by the IR source 6. Alternatively, the camera can use its electronics block 5 to adjust the focus automatically using the IR beam as would normally do without the adapter 10.

Light from the anterior chamber may reflect towards the camera 1 and saturate the array 3. To avoid this, light is linearly polarized using polarisers 14 and 14' and then sent via quarter wave plates 15 and 15'. Polarised light with orientation at 45 degrees from the waveplate axes will be transformed into circular polarized light. When light returns from the anterior chamber, the circular polarized light changes handedness and when going through the quarter wave plate 15" acquires a linear polarized direction perpendicular to that generated by the polarizer 14. The linear polarizer 14" oriented at 90 degrees eliminates the specular reflection from the anterior chamber. If the arrangement of wave-plates 15, 15' and 15" and polarizers 14, 14' and 14" are used, this has the disadvantage also of producing a polarization sensitive image from the eye fundus. Therefore, elements 15, 15' and 15" and 14, 14' and 14" may not be used all the time. Possible elimination of the anterior chamber reflection could be implemented in a different way by sending the beams from the optical sources, 4 and 6 slightly off-axis while maintaining the array 3 on-axis. It is also possible to shift the array 3 off-axis and use the beams from the optical sources 4 and 6 on-axis.

It should be obvious for those skilled in the art that the elements 14, 15, 19 as well as 14', 15' and 19' could be placed anywhere in the beam from the flash 4 or from the IR beam 6 respectively.

If the power from the flash 4 is of too large power for the eye, then an attenuator 16 is inserted into the beam from the flash.

In order to adjust the focus on the retina, depending on the camera used, different procedures are feasible. If the camera is equipped with automatic focus only, then the axial position of the lens 13 is manually adjusted in different positions by actuating on the translation stage 17 and the IR beam 6 is used, checking the image of the retina on the camera monitor 8. Alternatively, if the IR beam does not have sufficient power, several images are collected and their sharpness checked on the monitor 8 or on the PC, 50, connected to the electronics block 5.

If the camera can be set on manual focus, then the user can actuate on both the camera focus control set on manual via block 5, which controls the objective lens 21, and onto the stage 17 to move the focusing element 13, in order to obtain a sharp image under illumination provided by the IR beam 6. If the IR beam 6 is of insufficient optical power, then several images can be collected and the sharpness checked on the monitor 8.

Alternatively, the integration time of the camera can be increased to enhance its sensitivity and become able to employ the IR beam to produce a good signal to noise ratio image from the retina. This is a common feature for most of the commercially available cameras which can be used to enhance their sensitivity considerably.

Images are stored on the internal memory card 51, or sent directly to the PC 50 via the connecting cable or wireless connection such as blue tooth, 55.

The focusing elements and processing light elements of the optical sources of the conventional camera 1 are placed on adjustable supports to allow spatial lateral and height adjustment to accommodate different cameras on the market and be placed at corresponding distances from the camera axis to intercept the beams out of sources 4 and 6. Commercially available cameras present different formats, some cameras are ultra-slim and small, others at the higher performance end are larger. Mechanical adjustments could be provided in two or three or more versions to fit such variations from vendor to vendor and this will be indicated on the version of adapter 10 to be fabricated.

Spectroscopic Imaging

Spectroscopic analysis can be performed by collecting several images of the retina for each press of the shutter button 9 for a different filter 19. The filter can be changed manually. Alternatively, a micro-filter wheel can be used or an electrical controlled filter whose central wavelength band is advanced for each press of the shutter. To do this, a photodetector with driver 26 is used to advance the filter position in the spectral filter 19 via a counter for n filter steps, 138, where the control commands are sent along the line 128.

Details

The object may be the retina of a human eye or animal and the adapter is used to convey light from the retina towards the said commercially available camera through the eye pupil and the said source interface optics conveys light towards the retina through the eye pupil and where the said source optics interface and the adapter use waveplates and polarizers to operate like optical isolators to reduce the reflections from the anterior chamber of the eye.

The digital camera may be a colour camera where pixels in the said photodetected array are sensitive to three colours, r, g, b and where the flash source interface optics is equipped with a spectral filter unit to select three optical windows, r, g, b, each centred on the maximum of sensitivity of the colour segments r, g, b in the photodetector sensor, out of the spectral output of the flash source of the digital camera.

The camera may be equipped with an accessory mount for handling the adapter and the camera in front of the object.

The said accessory mount may be equipped with means to be attached to the object.

The accessory mount may be equipped with means to be held by an user.

The accessory mount may be equipped with means to allow stable manual scanning of the object by moving the adapter laterally and axially in respect to the object.

2. TIME DOMAIN EN-FACE OCT

Figure 2:
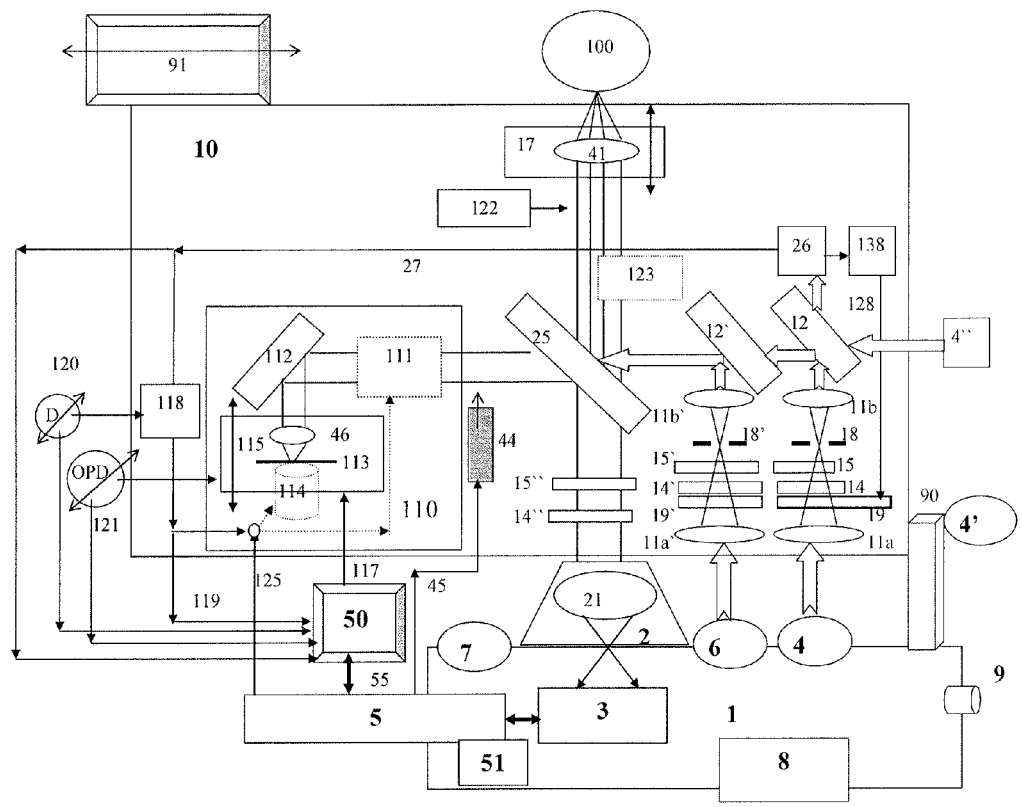
FIG. 2 shows a second embodiment of the present invention where a dedicated adapter uses a commercially available camera to acquire en-face OCT images from a fixed depth within the object.

FIG. 2 describes a second embodiment of the present invention. The adapter here is designed to transform the camera into an en-face OCT system. A low coherence interferometer is assembled using the flash 4, or the IR beam 6, as a low coherence source. Optical spectral filter 19 may be equipped with notch filters to reject narrow spikes of the flash source which deteriorate the correlation function of the interferometer. An optical splitter 25 divides the beams from the optical source, 4 or 6 or both into an object beam and a reference beam in a Michelson interferometer. In addition to the embodiment in FIG. 1, a reference path is added to create a reference beam to interfere with the object beam from the object 100. The reference beam is reflected by an optical path difference (OPD) adjusting block, 110. This is used to adjust the OPD value, i.e. the depth where the en-face image will be acquired from the object 100, considered the cornea or skin in the example, with light focused by a focusing element 41. It should be obvious for those skilled in the art that the embodiment could equally be used for imaging the retina if a suitable optical interface is added or the role of the convergent element 41 is accomplished by the eye lens.

Focus is achieved by using the manual or automatic focusing adjustment of the digital camera which moves objective 2 or using a supplementary translation stage 17 to move the focusing element 41.

The other function of the block 110 is image demodulation by inducing optical path modulation. In order to create an en-face image, according to principles of phase shifting interferometry, at least three frames need to be collected for three different OPD values, therefore the block 110 has to change the OPD in steps of $\lambda/3$, where $\lambda$ is the central wavelength of the optical spectrum of the source used, 4 or 6. Therefore, an optical path modulator, 111 is used. In order to alter the OPD, different possibilities exist, as illustrated in FIG. 2. An electro-optic modulator or a magneto-optic modulator, 111, with associated polarizer elements can be used under electrical signal control, as a phase modulator. Another possibility is for a mechanical oscillator, based on a piezostrictive or magnetostrictive element, 114, which suffers dimensional changes under electrical signal, to move the mirror 113 which returns the reference beam back to the optical splitter 25. If the adapter transforms the digital camera 1 into a microscope, then a Linnik configuration can be implemented in which case a supplementary converging element is used, 46 (preferably of the same focus power as that used in the object path, 41) in front of the mirror 113.

Alternatively, the block 110 can be assembled as a spectral scanning delay line. A spectral delay line uses a diffraction grating, a lens and a galvanometer scanner. The linear variation of phase versus optical frequency is introduced by tilting the galvanometer mirror behind a lens, where the galvanometer mirror is situated in the Fourier plane of the lens.

The adapter and the camera can be moved laterally along a sliding mechanism 91 to collect images or perform measurements from different parts of the object 100. The support 91 is also equipped with straps and adapting means which are customised to different types of objects, cornea of the human eye, vertical mount for imaging cornea of animals, microscope mounts for histology specimens or protecting supports in case objects of art are imaged with proximity sensors or other means to avoid contact, or other supporting means for used underwater or in harsh conditions. These adapting means are designed as extras and could be bought as accessories to the adapter to customise the adapter to a particular application.

An accessory mount can be devised to secure the adapter on the object, such as a patient when imaging skin.

An accessory mount can be devised to secure the adapter on the hands of the user when imaging paintings or working underwater.

The sliding mechanism can be provided with scales for accurate steps along rectangular directions and locking devices. The adapter carrying the camera is moved laterally, locked in place and then an acquisition process is triggered by the PC 50 or by pressing the shutter button 9.

2.1. Phase Shifting Interferometry

The camera is required to flash at least two or three times to collect two or three images for different OPD values. Some cameras can provide quick flashing, at least two or three are required, in a rapid fire sequence after the press of the shutter button 9. In this case, two or three frames are acquired and an en-face OCT image is produced in the PC 50 after downloading the two or three frames from the storage card 51 or after direct download.

The generation in succession of two, three or more electrical spikes to step the phase in the OPD adjustment block 110 is controlled by the electronics block 5 in the camera 1 along line 125.

In case the camera does not provide an electrical signal synchronous with the flash 4 nor with the shutter button, 9, then the adapter takes this role. To this goal, the adapter is equipped with a photodetector and spike shaper, 26, which under the control of the flash beam from the source 4, delivers a trigger signal via line 27, which actuates onto the OPD adjustment block, 110. This controls either the mechanical oscillator or piezo 114 or the optical modulator 111, which here is used as a phase modulator. Alternatively, the line 27 can supply spikes to the PC 50 which can actuate onto the block 110 via line 125.

To obtain another en-face image from a different depth from within the object, eye, skin, teeth or painting, the reference reflector position is changed accordingly by moving the translation stage 115, which holds the mirror 113.

Alternatively, the translation stage 115 could be equipped with a micro-motorised stage and controlled via an electronic interface along the line 117. If the block 110 uses a spectral scanning delay line as explained above, then the line 117 actuates on the galvo-scanner in the scanning delay line.

Intuitively, if a spectral scanning delay line is used, then three elements are required: (i) a galvo-scanner which takes the position of the mirror 113, (ii) a focusing element, a lens or a curved mirror which takes the place of the mirror 112 and (iii) a diffraction grating which takes place of the modulator 111.

The flash 4 or the IR beam 6 may have too large a bandwidth, which determines a too short coherence length. This leads to a too thin OCT en-face image. This may be altered by using a narrow spectral filter, 19 and 19', in front of the sources 4 and 6 respectively. This may also improve the tolerance of the interferometer in the adapter to dispersion. This may also be required for the phase shifting method efficiency. It is also known that the modulation efficiency of electro-optics and magneto-optic modulators depend on wavelength, and therefore a spectral filter, 19 and 19' may be found useful.

Shutter times of ms and sub-ms as well as flash duration of sub ms are ideal for avoidance of fringe washout. The transfer of images to memory or card 51 may be long, however the camera shutter can be opened with currently available technology for ms or sub-ms time to acquire a high visibility fringe signal.

Another function of filter 19 is that of rejecting or attenuating the narrow spikes in the flash emission, known being that these reduce the depth resolution in OCT. This is necessary when the flash lamp uses gases, such as the Argon or Krypton flash lamps. However, modern flash lamps use high power LEDs which exhibit an ideal white large band spectrum for low coherence interferometry measurements and OCT imaging.

In case the flash lamp is made from three powerful LEDs on the three fundamental colours, then the pinhole 18 is replaced by three different pinholes, one for each colour source, situated in a plane perpendicular on the optic axis starting from the centre of the flash 4. This will lead to deviation of colour beams within the object beam and deviation of the colour images on the sensor. This may be tolerated on the expense of larger transversal pixel size. As explained below, this may be tolerated in the angular compounding application for speckle reduction. Additionally, the three images could be shifted after acquisition for superposition.

Figure 3:
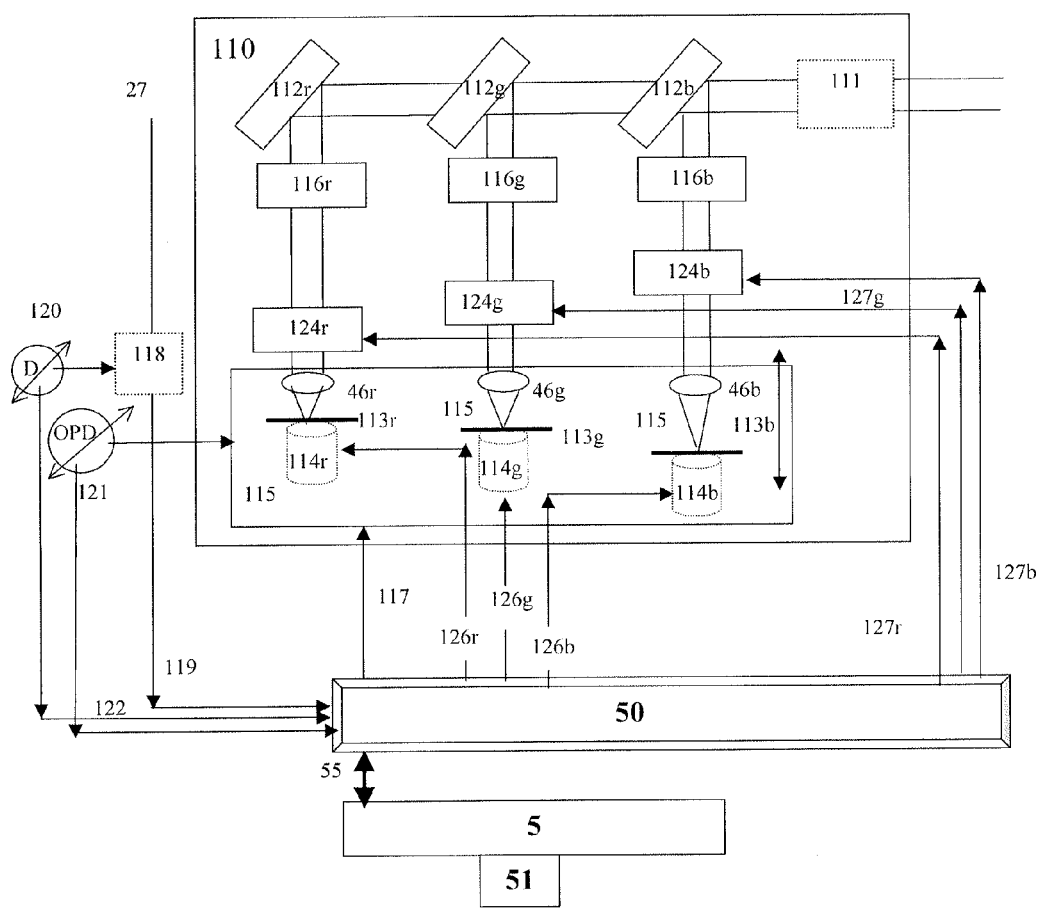
FIG. 3 shows an embodiment of the OPD adjustment block to operate in conjunction with a colour camera.
Figure 6:
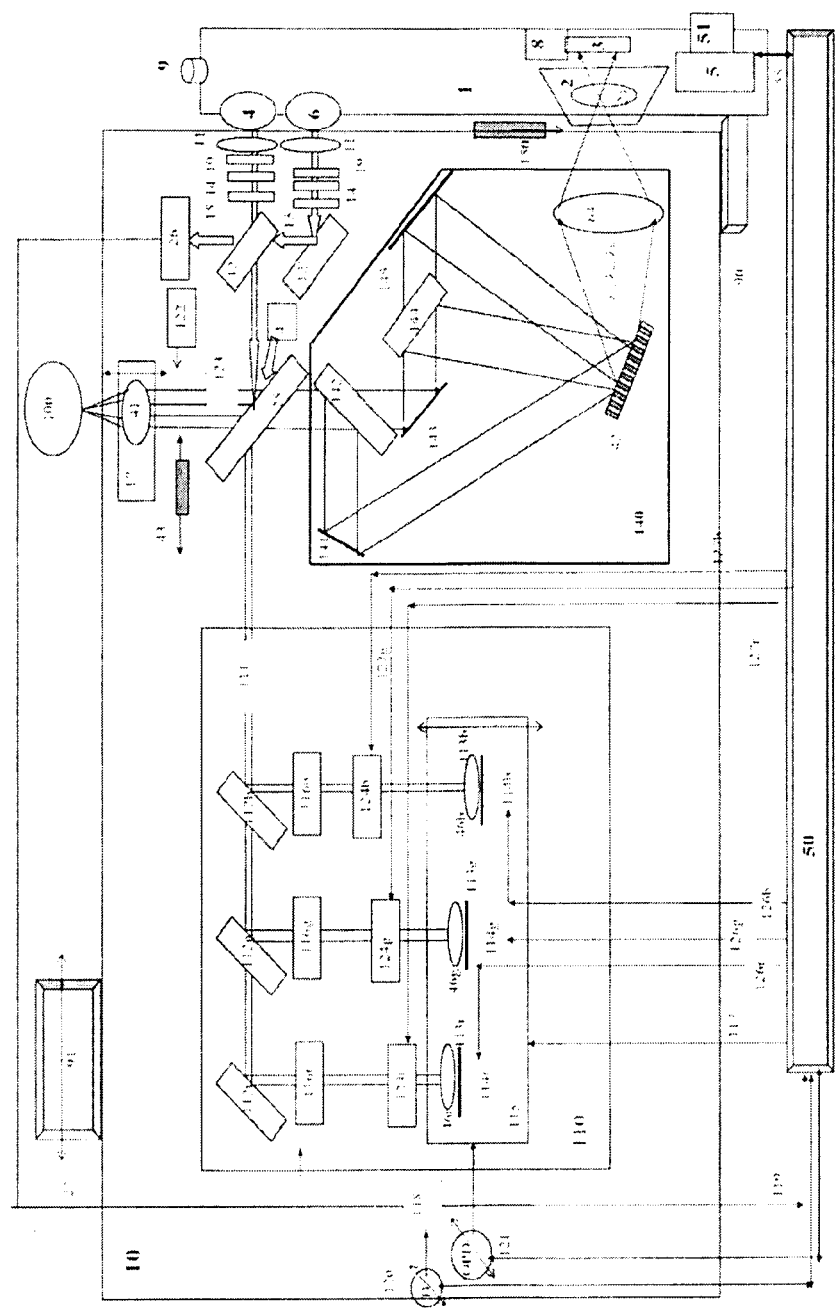
FIG. 6 shows a fifth embodiment of the present invention to perform CS-OCT using a multiplexer to superpose all spectral bands on the same pixels of the photodetector array.

Alternatively, the beams from the three point sources corresponding to the three pinholes could be brought to coincidence using micro dichroic filters and splitters using principles used in the construction of the block 110 in FIG. 3 or of the multiplexor 140 in FIG. 6.

In some of the applications described here where the colour parts of the sensor are used, the optical source is conditioned to launch its large spectrum into three spectral bands of suitable width centred on conveniently chosen central wavelength as to ensure a good cross talk between the colour parts of each pixel. Depth resolutions in the range of 10-20 microns are achievable with bandwidths in the range of 10-30 nm. Therefore, for good cross-talk, the width of the three spectra will be limited to let us say 20 nm and separated by 20 nm, this gives a 100 nm emission spectrum. The flash sources are sufficiently strong and require attenuation for safety. Creating gaps in the spectra between the colour components will lead to the necessary power reduction. Flash sources cover more than 200 nm band in the spectrum and the division of their spectrum in three bands of 20 nm each is possible. To ensure similar depth resolution, the filters to trim the spectrum could be conveniently adjusted to $$\frac{\lambda_r^2}{\Delta\lambda_r} \approx \frac{\lambda_g^2}{\Delta\lambda_g} \approx \frac{\lambda_b^2}{\Delta\lambda_b} \tag{1}$$

where $\lambda_r, \lambda_g, \lambda_b$ are the central wavelengths of the three bands and the $\Delta\lambda_r, \Delta\lambda_g, \Delta\lambda_b$ are the bandwidths of the three peaks left in the source emission spectrum after spectral filtration.

2.2. Collecting a Stack of En-Face OCT Images from Different Depths.

Different procedures are possible, depending on the camera. If the camera is equipped with an input which accepts pulses for controlling the moment when images are taken (external shutter), or if it has a remote control for the time of image taking, or if it is equipped with an interface, normally a USB connector, then the PC 50 takes control of the acquisition. For each required depth, via the control line 117, a program in the PC 50 controls the OPD in the interferometer by moving the stage 115 or via line 125 controls either the vibrator or piezo 114 or the phase modulator 111 or both. If the role of subwavelength shifts is left to the piezo 114 and phase modulator 111, then the stage 115 is used for bigger steps, D. The stage 115 is moved in steps, D, comparable with the coherence length of the optical source, 4 or 6, estimated as a few microns. For example, the block 110 is stepped in incremental steps of D=20 microns, and for each such step, the OPD is changed in small steps of $\lambda/n$ using the piezo 114 or/and phase modulator 111, with a typical value for n=3. For n=3, the signal at each pixel is obtained from three values, $I_1$, $I_2$ and $I_3$ of the same pixel obtained for the 3 steps by:

$$s=\sqrt{(I_1-I_2)^2+(I_1-I_3)^2+(I_2-I_3)^2} \tag{2}$$

If n=3, then for a central wavelength of $\lambda$=750 nm, the small steps are 250 nm each.

If camera does not have an electrical input for controlling the shutter, nor it outputs any electrical signal when the shutter button is pressed, then a $2^{nd}$ procedure is used, as described immediately below. Several groups of n images are acquired for each manual press on the shutter button, 9, using impulses created by photodetector 26. If this will continue for any press of the shutter button 9, then a too dense collection of images would be obtained. Therefore, a counter, which after every set of n pulses, advances the OPD by a selected value, D. This could be implemented with an extra block, a counter 118, which clocks up to n=3, 4 or 5, depending on how many steps are collected for phase shifting interferometry, where the counter block 118 itself changes the OPD by a larger value D, after a number of steps n. Alternatively, the counter block 118 communicates with the PC via line 119, and an input-output board in the PC 50 works out based on a program, the amplitude of the electrical signal to be sent to the OPD block 110 to modify the OPD by a D step.

The user has the possibility to choose the values D of steps between the images in the stack, as well as the current value of OPD, as shown by knobs 120 and 121 respectively. They could act either on the PC 50, which then controls the stage 115 via line 117 and vibrator 114 and phase modulator 111 via line 125. Knobs 120 and 121 could also control block 110 directly.

Alternatively, the function of the counter 118 can be taken by the PC, 50, line 27 itself can be sent directly to the PC to work out small steps to be applied via line 125 and big steps D via line 117.

According to the procedure and embodiment described above, such OCT images can be produced at low cost. Cameras of 5 Mpixels are now commercially available for less than 200 pound. Their flash can stand over 10000 events. Several photographic flash optical sources and flash sources incorporated into digital camera box can flash a quick sequence of three flashes or more in 1 s and collect 3 images or more in synchronism. This could ideally be used with the adapter as described above to produce an enlace OCT image using phase shifting interferometry principle with n=3 steps (or with n=2 steps applying Hilbert transformation). In this case, line 27 can act upon block 110 to produce the small steps of subwavelength values $\lambda/n$ and after each press of the shutter button 9, the stage 115 is advanced manually or via the PC control 50.

If the camera does not have the capability of rapid fire of sequential flashes, then the shutter 9 has to be pressed manually for n=2 or 3 times at least to acquire interference images which are later processed to produce a single OCT en-face image from a given depth.

2.3. Phase Shifting Using the Colour Sensor Parts in the Camera

In a different embodiment, the three steps required for phase shifting interferometry are produced using a different OPD adjusting block, 110, and employing the three colour channels in any colour CCD camera, as shown in FIG. 3. The OPD adjustment block 110 has three optical paths separated by dichroic filters. Let us suppose that the optical spectrum of the flash source 4 can be divided into three windows, r, g, b, where r means the longest wavelength window, g an intermediate window and b the shortest wavelength window. They could be associated to the three fundamental colors of the spectrum, red, green and blue. For instance, the three windows could be described by: r=570-900 nm, g=500-570 nm and b=450-500 nm. The splitter 112b is a cold mirror which reflects the window b and transmit the other two band windows, the splitter 112g is a cold mirror which reflects band g and transmits band r and 112r could be a simple mirror. It should be obvious for those skilled in the art that the same function can be equally implemented with hot mirrors, in which case the first reflected beam is in the r band and for the last band, of shortest wavelength, the filter is a simple mirror. The spectral selection is obtained in FIG. 3 in reflection. For those skilled in the art, it should be obvious that hot mirrors and cold mirrors could equally be used in transmission and selection of suitable cold and hot mirrors can also be practised.

Two Possible Adjustments of Phase Shifts are Possible as Described in 2.3.1 and 2.3.2:

2.3.1. A Different Phase Shift Per Each Spectral Window

Waves within each spectral window r, g, b travel along independently adjustable path lengths using mirrors 113r, 113g, 113b respectively. Their optical paths are adjusted in such a way, that for $\lambda_R$ the OPD is zero, for $\lambda_G$ the OPD is $\lambda_G/3$ and for $\lambda_B$ the OPD=2 $\lambda_B/3$. It should be obvious for those skilled in the art that other combinations are equally feasible, where the OPD is zero for $\lambda_G$, the OPD is $-\lambda_R/3$ and for $\lambda_B$ the OPD=$\lambda_B/3$. Each spectral window channel in the camera will be sensitive to the respective color returned in the object arm from the object, 100, interfering with the similar color returned from the respective reference path. In this way, three interference frames are provided on the three colors. For each pixel in the CCD camera, three signals are collected for the three colours. These are used to produce the demodulated en-face OCT image. For each pixel in the photodetector array, let us denote $I_r$, $I_g$, and $I_b$, the intensity of the photodetected signal provided by each colour part of that pixel. The following quantity is evaluated as:

$$s = \sqrt{(I_r - I_g)^2 + (I_g - I_b)^2 + (I_r - I_b)^2} \quad (3)$$

If the point in the depth is outside coherence, all values are the same and the result is zero. If interference takes place, then the quantity in (3) approximates the amplitude of the interference signal.

Alternatively, more than 3 spectral windows and steps for phase shifting interferometry can be implemented. For instance for 5 steps, the block 110 in FIG. 3 is equipped with two more filters to separate signals in a band between b and g and a band between g and r. For these extra two signals, a photodetected signal $I_{bg}$ is constructed by compounding the two intensities $I_b$ and $I_g$, respectively, a photodetected signal $I_g$, is constructed by compounding the two intensities $I_g$ and $I_r$. Equation (3) becomes:

$$s = \sqrt{(I_r - I_{rg})^2 + (I_{rg} - I_g)^2 + (I_g - I_{gb})^2 + (I_{gb} - I_b)^2 + (I_b - I_r)^2} \quad (3a)$$

All the intensities, $I_p$ with p=r, g, b, gb, rg above are normalised such that for a mirror as object and when the OPD is outside coherence, all $I_p$ are equal.

Three Dimensional Imaging

C-scan OCT images can be collected at different depths by repeating the process above for a different OPD adjusted by actuating on the stage 115 or on the spectral scanning delay line in the block 110 to adjust the OPD in steps larger than the coherence length associated to the individual spectral bands. The repetition can be actuated manually by pressing the shutter button 9 or if the camera is equipped with the rapid fire feature, can be performed automatically up to the maximum number of flashes allowed by the flash source 4. If f=10, then 10×3 interference images are collected, from each set of three images a C-scan OCT image is generated. By using Hilbert transformation, two steps are enough and therefore the number of images required becomes 10×2. In case the camera does not output pulses for each flash, then the data acquisition can proceed using the photodetector 26 (in FIG. 2) and counter 118. In case the colour camera has m colour sensors and the flash can burst f times in sequence, then a number of mf interference images are collected and from each set of m images a C-scan image is produced at each depth.

2.3.2. Practising the Same Step of Phase Shift in all Colour Bands

In this case, each mirror 113r, 113g and 113b in the block 110 is actuated with a respective piezo 114r, 114g and 114b to implement exact steps for the corresponding central wavelengths, $\lambda_r$, $\lambda_g$ and $\lambda_b$. The stepping at exact values of zero in all three bands, then at $\lambda_r/3$, $\lambda_g/3$ and $\lambda_b/3$ and next for $2\lambda_r/3$, $2\lambda_g/3$ and $2\lambda_b/3$ is provided via control lines 126r, 126g and 126b respectively.

Extending the Depth Range or Increasing the Speed of Operation

Another function of the embodiment in FIG. 2 equipped with the block 110 in FIG. 3 is for covering an extended range of depths in less time. Let us consider that the target has similar spectral properties, for instance in profilometry of a corrugated surface extending in height variations over R=300 microns. In that case, each colour of the sensor and the associated emitted spectrum from the optical source, 4 or 6 can be used to cover ⅓ of the range R, i.e. R/3=100 microns. If the coherence length of the associated spectral window bands has a similar value of $l_c$=20 microns, then M=R/(3$l_c$)=5 steps. Using a D=20 micron differential step applied via block 110 will collect for each spectral window sufficient data to cover R/3=100 micron, and in fact images from a whole depth of 300 microns is collected. Initially, the mirrors 113r, 113g and 113b are adjusted for the OCT in green to start at an OPD longer (or shorter) than that of the OCT in blue by R/3=100 microns and for the OCT in red to start at an OPD longer (or shorter) than that of the OCT in blue by 2 R/3=200 microns. In 5 steps, 15 C-scan images are acquired when using the rapid fire procedure of 3 flashes. Three phase steps are imprinted as explained above to acquire 3 interference images which are subsequently used to construct a C-scan OCT image. To perform this function, the three spectral lengths of the block 110 have to be stepped with corresponding sub-wavelength values 0, λ/3 and 2λ/3 for each respective band.

Evaluating the Curvature of Curved Objects

If the object is a sphere and profilometry is required, or the object 100 is the cornea of an eye and the curvature is required, the procedure explained above to increase the depth range is applicable to produce profilometry or curvature measurement. Let us say that the three colour channel OCT systems are set via the length of the three reference paths r, g and b in the embodiment in FIG. 3 to OPD, OPD+d and OPD+2 d, where d is comparable with the coherence length, considered approximately the same for all three spectral bands r, g, and b. Then three C-scan images at three different depths will be obtained, corresponding to the three values of OPD. If we are to consider the contour of the cornea image only in the C-scan image, representing the discontinuity in the index of refraction between air and the cornea tissue, then three circular contours of ascending size will be obtained as the depth increases from one channel to the other. Knowing the value d, the curvature of the cornea as well as the distance of the cornea apex from the OCT system could be inferred by simple Mathematics knowing the d value, as described in US Patent Application, 20080170204, Method and apparatus for determining the shape, distance and orientation of an object, with the difference that the colour sensitive parts are used for each delay. To obtain each OCT image in each of the spectral band, three phase steps are imprinted as explained above to acquire 3 interference images. To perform this function, the three spectral lengths of the block 3 have to be stepped with corresponding sub-wavelength values 0, $\lambda/3$ and $2\lambda/3$ for each respective band.

Speckle Reduction

A microscope slide 123 can be inserted halfway into the object beam before the final lens 41 as shown in dashed line in FIG. 2, of such a thickness as to determine an optical delay larger than the thickness of the object to be measured. Let us say that the object is a superposition of layers of paint and exhibits a thickness R=0.7 mm. In this case, the delay introduced by the plate 123 is adjusted to be d=1 mm in relation to the one way rays going through the other side of the beam non intercepted by the plate. The OPD in the three channels, r, g, and b in the reference paths in FIG. 3 are adjusted 1 mm apart. For instance, the r channel is adjusted to have a reference path length longer by 1 mm than the green channel and the b channel to be shorter by 1 mm than the reference length of the g channel.

Three C-scans are obtained, one for each colour. One colour is used to collect light which encounters the plate delay once, delay d (rays which go through air and in the way back encounters the plate 123, or rays which go through the plate and in the returning path skip the plate), in which case the corresponding colour reference path is adjusted to d. The second colour is adjusted to match the rays which do not intercept the slide 123 at all, in which case the corresponding colour reference path is adjusted on zero, and the third colour channel is adjusted to match the rays which go through the slide 123 twice (towards and backwards from the object 100), in which case the corresponding colour reference path is adjusted to 2 d. The three C-scans originate from the same depth but are produced at three different incidence angle of the incoming rays and when they are superposed in the PC, speckle will be reduced. The basic idea is that rays in the three channels enter the object under different angles and by angular average, speckle is reduced. Here, the angular incidence of the ray on the object is encoded on wavelength.

Three phase steps are imprinted as explained above to acquire 3 interference images. To perform this function, the three spectral lengths of the block 3 have to be stepped with corresponding sub-wavelength values 0, $\lambda/3$ and $2\lambda/3$ for each respective band.

Spectroscopic En-Face OCT

Another function of the embodiment in FIG. 2 equipped with the block in FIG. 3 is that of providing spectroscopic en-face OCT. This function is useful when the object exhibits different properties (index of refraction, reflectivity, scattering or absorption, polarization, etc.) variable versus wavelength. Such a case is that of measuring the concentration of macular pigments in the eye or for oximetry of the eye and skin. For such an operation, each colour sensor and the associated band emitted by the optical source are used to provide OCT information about the object in that band. This means that at least two or three phase steps are required before a group of two or three different spectral band C-scans are created. At each step, two or three phase steps are imprinted as explained above to acquire 3 interference images. To perform this function, the three spectral lengths of the block 110 have to be stepped with corresponding sub-wavelength values 0, $\lambda/3$ and $2\lambda/3$ for each respective band, where the OPD in the three spectral bands selected by block 110 are substantially the same.

In the process of adjustment, a few shots are collected checking the adjustment of the depth. Using the knob 121, or manually adjusting the position of the stage 115 or acting on the stage 115 via PC control 117, the depth where the acquisition will start for 3D imaging is adjusted. Then, a number of 3P acquisitions steps are performed under the control of the PC. For phase shifting interferometry, as explained before, two procedures can be implemented. In case the camera does not output any electrical signal to sense the shot, then the photodetector 26 is used to automatically advance phase steps in all three channels and at every 3 steps to return the piezo 114 to zero (or two steps of half wavelength when using Hilbert transformation), or move the stage 115 in subwavelength steps, by actuating on the PC50 via line 119 which will send voltages to the piezo 114r, 114g and 114b via the electronic interface 5.

Polarisation Sensitive En-Face OCT

Light is linearly polarized by one of the elements 14, 15 or 19 (14', 15' or 19') and sent towards the object 100 via a wave plate, preferably at 45° from the axes of a quarter wave plate 122. Elements 116r, 116g and 116b in the three reference paths are polarisation selectors. Let us consider the object 100 as an uniaxial birefringent crystal. In this case, for instance 116r could be a half-wave plate oriented at 22.5° for the central wavelength of the red spectral band, while 116g is a zero degree waveplate or none is placed in the green reference channel. Linear polarised light traversing the waveplate 116r twice will incur a rotation of 90 degrees. In this case, the OCT C-scans delivered by the red and green parts of the sensor 3 represent orthogonal polarization signals, H and V respectively. Other combinations are equally possible. By evaluating:

$$s = \sqrt{H^2 + V^2} \text{ and } \varphi = \tan^{-1}\frac{H}{V} \quad (4a, b)$$

a polarization insensitive C-scan is obtained from the signal s and the orientation of the birefringence axis at the respective depth where the C-scan images are collected is given by the angle φ. Obviously, two or three phase steps as explained above are required to obtain the signals H and V.

The blue channel could be equipped with another waveplate at a different angle adding another point on the Poincare sphere and allowing a further improve in the evaluation of signals s and φ.

Here polarisation sensitive information from the object is encoded on wavelength using a colour digital camera.

Three phase steps are imprinted as explained above to acquire two or three interference images. To perform this function, the three spectral lengths of the block 110 have to be stepped with corresponding sub-wavelength values 0, $\lambda/2$ when using two steps and Hilbert transformation and 0, $\lambda/3$ and $2\lambda/3$ when using standard three phase shifts procedure, for each respective band.

2.4. Sequential OCT/Confocal Imaging

To view the object only and perform imaging, a screen 44 can be introduced into the reference beam. This could be a flipping screen mechanically or electrically controlled by PC 50 under line 45.

2.5 Further Details

In more detail, the embodiment relates to a camera adapter based optical imaging apparatus to image an object which consists in an adapter and a commercially available digital camera, where the digital camera is equipped with at least an optical source, a photodetector array and a manual shutter button and where the said adapter makes use of the optical source equipping the said digital camera to illuminate the object observed as well as ensure that light from the optical source reflected from the object is transferred to the said digital camera via the adapter and makes use of the photodetector array to produce depth resolved information about the topography of the object and about its internal structure.

The said adapter may incorporate a low coherence interferometer.

The digital camera may be equipped with a flash lamp normally used to illuminate the scene photographed by the said digital camera and its output light is conditioned in its spatial distribution and beam diameter by the said adapter using a flash source interface optics to illuminate the object.

The digital camera may be equipped with an IR beam used normally to illuminate the scene photographed for aiding automatic focus and where the said optical source is the output light resulting by conditioning the IR beam in its spatial distribution and beam diameter by the said adapter using an IR beam source interface optics to illuminate the object.

The low coherence interferometer may contain at least one beamsplitter which divides the light from the said optical source into an object beam conveyed to the said object and a reference beam towards an optical delay block and where light from the object is returned via the adapter and the beamsplitter to interfere with light from the optical delay block on the said photodetector array which acquires an interference image for each press of the shutter button and where the optical delay block is equipped with means to adjust the length of its path measured roundtrip from the beamsplitter, and at each press of the shutter button the optical delay path is adjusted to a new value.

The means of altering the reference path may be controlled by signal delivered from the digital camera at each press of the shutter button.

The means of altering the reference path may change the length of the reference path by a subdivision, $\lambda/n$ of the central wavelength $\lambda$ of the spectrum of the said optical source and which brings the reference length to the initial value after n such steps and where a C-scan OCT image is evaluated by combining the n acquired interference images.

The camera adapter may be additionally equipped with a photodetector which senses the presence of light from the said optical source, photodetector which drives a counter and where the means of altering the reference path is controlled by signal delivered by the said photodetector in small steps and by the said counter in big steps, where the small steps are cyclical and the big steps are cumulative, where the small steps cycle is $0, \lambda/n, 2\lambda/n, \ldots (n-1)\lambda/n$ where $\lambda$ is the central wavelength of the spectrum of the said optical source and where for each flash of the optical source, an interference image is collected and stored, and where after n flashes the counter determines that a cumulative OPD=D step is imprinted to the said delay adjustment block before acquiring the next set of n interference images from a different depth incremented by D in the said object in comparison with the previous depth and where a C-scan OCT image is evaluated at depths multiple of D for each set of consecutive n acquired interference images.

The sensor array in the digital camera may be a colour array which delivers signals from each pixel corresponding to spectral components in three bands, r, g, b, centred on respectively $\lambda_r, \lambda_g, \lambda_b$ as part of the spectrum of the said optical source and the optical delay block operates spectral selection in the three separate reference paths, r, g, b equipped with three r, g, b arms tuned on the three spectral different bands, the optical delay block returning three optical r, g, b waves to the said beamsplitter and where each reference path r, g and b can be independently adjusted in relation to the other two.

The means for adjusting the path length in the said optic delay block may consist in a spectral scanning delay line equipped with at least a dispersing (diffraction) element, a focusing element and a tilting mirror whose tilt can be actuated via electrical signal input.

The three spectral reference paths r, g, b may be adjusted to generate an optical path difference between each reference path length and the object path length of 0 $\lambda_i$, $\lambda_j/3$ and $2\lambda_s/3$ where i, j and s could be any set of permutations of r,g,b and where three interference images are generated by the said colour sensor array, one for each band r, g, b, with $I_r$, $I_g$, and $I_b$, the intensity of the photodetected signal provided by each colour part of the said camera pixels and where a C-scan OCT image is assembled for each pixel using the values delivered by the colour parts of the same pixel in the three interference r, g, b images evaluated as: $s=\sqrt{(I_r-I_g)^2+(I_g-I_b)^2+I_r-I_b)^2}$, where such OCT image is generated after pressing the said shutter button once.

The three spectral reference paths r, g, b may be adjusted to generate: at the first press of the said shutter button, an optical path difference between each reference path length and the object path length of zero, the adapter collecting intensities $I_{1p}$, with p=r,g,b,
at the second press of the shutter button, OPD values of $\lambda_r/3$ in the r reference path, $\lambda_g/3$ in the g reference path and of $\lambda_b/3$ in the b reference path, the adapter collecting intensities $I_{2p}$, with p=r,g,b,
and at the third press of the shutter button, OPD values of $2\lambda_r/3$ in the r reference path, $2\lambda_g/3$ in the g reference path and of $2\lambda_b/3$ in the b reference path, the adapter collecting intensities $I_{3p}$, with p=r,g,b and where three C-scan OCT images of $s_p=\sqrt{(I_{1p}-I_{2p})^2+(I_{1p}-I_{3p})^2+(I_{2p}-I_{3p})^2}$ on each pixel with p=r, g, b are assembled for each colour r, g, b of the colour parts of the pixels in the said photodetector sensor array from the three interference images acquired for the three presses of the shutter button.

The digital camera optical source can fire three flashes in sequence from the said optical source at one press of the shutter button and where the intensities $I_{1p}$ are collected using the first flash, intensities $I_{2p}$ are collected using the second flash and intensities $I_{3p}$ are collected using the third flash automatically.

In order to produce a C-scan OCT image of less speckle, the adapter additionally uses a microscope slide of thickness providing an optical delay d for the rays going through it in comparison with the rays through air, plate which is introduced halfway through into the object beam and the spectral reference paths r, g, b in the reference block are adjusted in steps of d For polarisation imaging, each spectral path r, g, b in the optic delay block is provided with a polarisation element imprinting a different polarisation characteristic to each reference wave returned to the beamsplitter and where the said polarisation element is chosen from the category of linear polarisers or waveplates.

For curvature evaluation, the three spectral reference paths are initially adjusted on 0, d and 2 d, where d is larger than the coherence length corresponding to the individual bands and where phase shifts are applied to each path in the optic delay block to generate a C-scan OCT image at 0 depth in the first band, a C-scan OCT image at d depth in the second band and a C-scan OCT image at 2 d in the third band when the first, second and third band could be any of the r, g or b band and by superposing the three C-scan OCT images in one compound frame and measuring the differential distances between different contours such created in the compound frame, evaluate the curvature of the object surface.

3. CHANNELED SPECTRUM OCT

Figure 4:
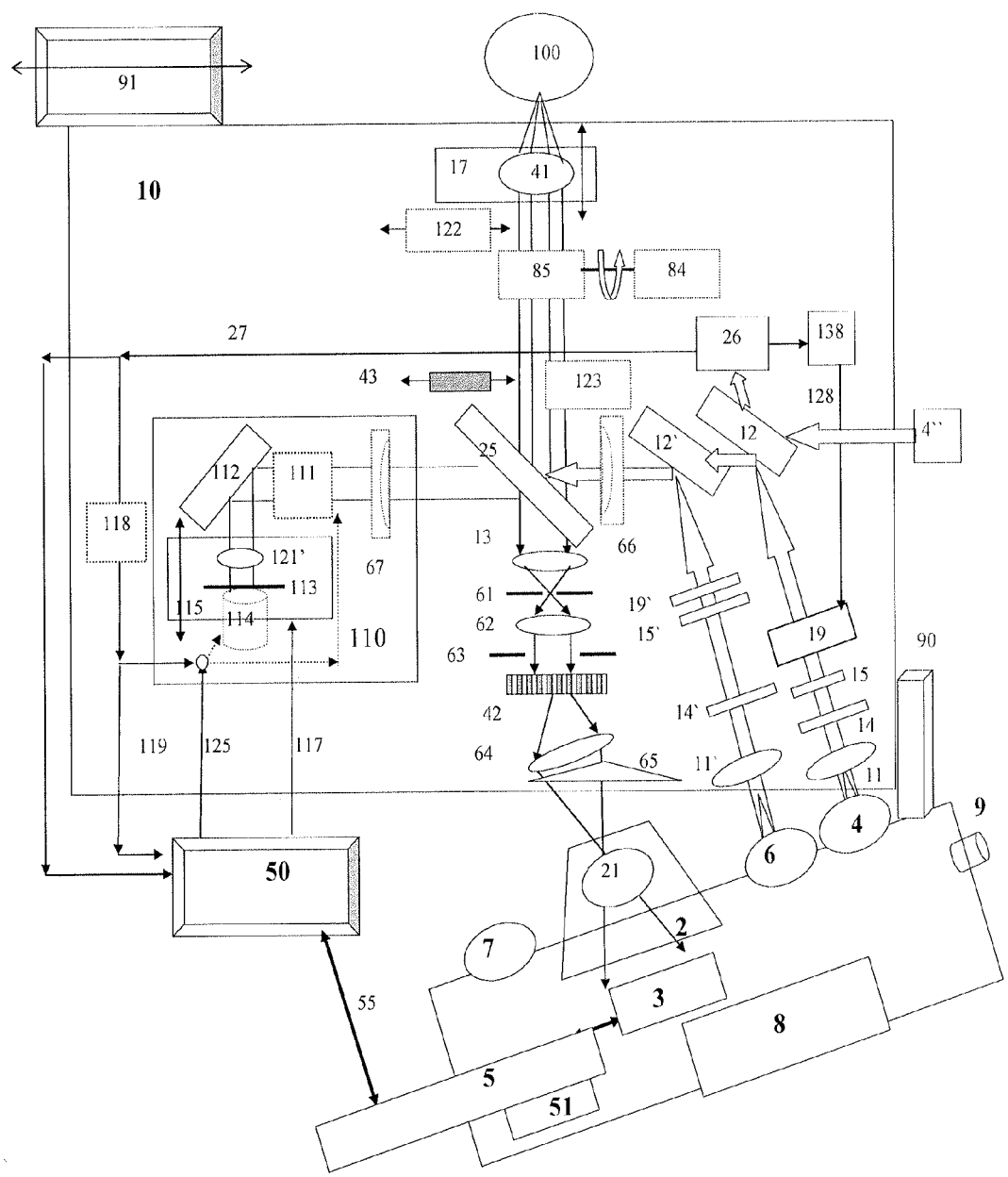
FIG. 4 shows a third embodiment of the present invention where a dedicated adapter uses a commercially available camera in a CS-OCT set-up to obtain an A-scan or a B-scan OCT image from the object.

Another embodiment of the present invention is shown in FIG. 4. Here, the adapter 10 transforms the camera into a channeled spectrum OCT system which can produce A-scans or OCT cross sections images (B-scan images) from the object, 100.

The key element is an optical dispersing component 42, which could be a prism or a diffraction grating, preferably a diffraction grating in transmission for its small volume and high dispersing power.

Phase shifting interferometry is no longer required and therefore the modulator 111 and piezo 114 may not be necessary, unless complex Fourier transform is evaluated as disclosed below.

1D OCT images, A-scans reflectivity profile are obtained along the spectral decomposition direction of the camera. Preferably, a number of pixels larger than 512 should be set along the dispersion direction, as this number multiplied by a quarter of the coherence length of the optical source determines approximately the depth range. The direction of pixels perpendicular to the spectral decomposition direction has little use here. Advantageously however, as the aberration of the optics lead to extended diffracted spots, more than one line of pixels of the 2D sensor array 3 should be collected (binned), this also results in enhanced sensitivity and increased speed. In the case of 3/2 camera ratio format, preferably the X direction (with the largest number of pixels), or the direction with the larger number of pixels should be oriented along the spectral decomposition direction, which in FIG. 4 is in the plane of the drawing.

To convey the light from the interferometer to spectral analysis via the dispersing element 42, a spatial filter 61, a converging element 62 and another spatial filter 63 may be used. To convey the dispersed light from the dispersing element 42, through the camera lens 21, a supplementary converging element 64 may be required. In case the focusing element 21 is detachable, other converging elements configuration may be used according to means known in the art. In order to generate a linear distribution of the output sensor 3 versus wave-numbers, a supplementary dispersing element, 65 may be used, as described in the paper "Fourier domain optical coherence tomography with a linear-in-wave number spectrometer", by Chilin Hul, and Andrew M. Rollins, published in Optics Letters, Vol. 32, No. 24, 2007, pp. 3525-3527, otherwise the linearization in wave-numbers is produced by software means in the PC 50 after download of the images from the interface 5.

Converging elements above could be any lenses or curved mirror. Dispersing element 65 could be a prism or a diffraction grating.

Focusing elements 11 and 11' include schematically the spatial filtration provided by two focusing elements 11a, 11b and the pinhole 18, respectively the elements 11a', 11b' and 18' as detailed in FIGS. 1 and 2 but now shown here.

Typical applications are measurement of the thickness of thin objects, such as cornea, paper, object of arts, the depth of scratches of interest in forensic analysis, etc. The optical path length of the anterior chamber of the human eye or of the whole eye if measured can provide important information on the health state of the human. It is known that the sugar content in the blood is also reflected in the eye. Therefore, by measuring optical path lengths in the eye, the content of sugar or of other constituents can be estimated. The optical path length is the product of the geometrical path by the index of refraction, and this is what is altered by chemical constituents, such as sugar. As sugar is also optically active, polarisation measurements can be added for enhanced accuracy by using different colour parts of the sensor as described above using reference paths customised for different polarisation states. Such a system using the adapter and a camera can replace the invasive method used today by diabetics who regularly prick their fingers.

Tear film thickness can be evaluated as well as information on dry eyes can be obtained using OCT A-scans.

As several cameras are now commercially available which are water proof, a compact system can be assembled to perform under water imaging, for instance to investigate the integrity of translucent machinery components or art objects. Black and white as well as colour cameras can be adapted, in which case a grey scale is obtained by known means of summing or weighting the contributions of the three spectral sensing parts.

3.1. Complex Channeled Spectrum OCT

Although phase shifting interferometry used by the embodiment in FIG. 2 is no longer necessary for CS-OCT, it could still be conveniently used for elimination of mirror terms. If OPD=0 is placed inside the object 100, mirror terms will distort the image, due to the fact that the same channeled spectrum results for positive and negative OPD values of the same modulus value. The same principle of phase shifting interferometry, with three subwavelength small displacements could be employed to eliminate the mirror terms. Different solutions are possible, such as using at least three subwavelength shifts employing the piezo or magneto-strictive element 114, or using a frequency shifter as described in the "Heterodyne Fourier domain optical coherence tomography for full range probing with high axial resolution", by A. H. Bachmann, R. A. Leitgeb, T, Lasser, published in 14(4), Opt. Express (2006) 1487-1496. Three phase shifts can advantageously be introduced using the embodiment of the block 110 in FIG. 3 which can replace the simplified block 110 shown in FIG. 4 for those objects which do not present spectral dependence of reflectivity nor spectral dependence of any other parameters involved in signal generation. In this case, the three channels, r, g, b can simultaneously provide interference signals which can conveniently be combined to eliminate the signal at zero frequency as well as the mirror term. Three A-scans are acquired using the r,g,b components of the RAW image provided by the camera. In principle, using three phase steps is sufficient to assemble complex Fourier transform and double the depth range of CS-OCT.

Similarly, using a frequency shifter as the optical modulator 111, the channeled spectrum is modulated with the signal applied to 111. For instance, reading the camera twice during a period of the signal applied to 111, delivers a cycle of modulation of the channeled spectrum. Signal applied to 111 can be sinusoidal of frequency 1 kHz and camera read in 0.5 ms. This can be achieved by collecting two shots at 0.5 ms apart. Some specialised camera can acquire two images during a single flash burst. In this case, the sequence of data trigger can be applied to 111, to apply max voltage for the first data acquisition step and applying zero voltage or minus voltage during the second data acquisition step. The flash duration is adjusted to last sufficiently long to allow this procedure. In the same way, by applying subdivisions of the voltage to 111 in synchronism with data acquisition steps, more than two images can be collected per modulation cycle. The images so collected are subsequently used to provide full range FDOCT B-scan images with elimination of mirror terms. This procedure can conveniently be combined with that using the three colours in the sensor 3, which together with different waveplates (phase shifts) can provide more points and respectively as many images which subsequently could be manipulated to produce a better full range B-scan image.

Polarisation Sensitive A-Scanning

Light is linearly polarized by the polariser 14 and rotated by the half-wave plate 15 for the flash source and polariser 14' and rotated by the half-wave plate 15' for the IR beam and sent towards the object 100 via a quarter wave-plate 122, preferably at 45° from its axes to launch circular polarised light towards the object. The three OPD values for the three path length of the spectral bands r, g, b are adjusted essentially the same using the mirrors 113r, 113g and 113b in the embodiment of the block 110 in FIG. 3 which can be incorporated into the embodiment in FIG. 4. Elements 116r, 116g and 116b in the three reference paths are polarisation selectors. Let us consider the object 100 as a uniaxial birefringent crystal. In this case, for instance 116r could be a half-wave plate oriented at 22.5° for the central wavelength of the red spectral band, while 116g is a zero degree waveplate or none is placed in the green reference channel in which case the OCT A-scans delivered by the red and green parts of the sensor 3 represent orthogonal polarization signals, H and V respectively. Other combinations are equally possible. By evaluating:

$$s = \sqrt{H^2 + V^2} \text{ and } \varphi = \tan^{-1}\frac{H}{V} \quad (5a, b)$$

a polarization insensitive A-scan is obtained from the signal s and the orientation of the birefringence axis along the depth is given by the angle $\varphi$.

The blue channel could be equipped with another waveplate at a different angle adding another point on the Poincare sphere of the object and allowing a further improve in the evaluation of signals s and $\varphi$ versus depth. It should be obvious for those skilled in the art that other combinations of plates 15 (15'), 122 and 116r, 116g and 116b are possible to obtain three or more polarisation data values.

Speckle Reduction

A microscope slide 123 as shown by the dashed line in FIG. 4 can be inserted half-way through into the object beam before the final lens 41 of such a thickness as to determine an optical delay larger than the thickness of the object to be measured. Let us say that the object is a superposition of layers of paint and exhibits a thickness R=0.7 mm. In this case, the delay introduced by the plate 123 is adjusted to be 1 mm for the rays going through in comparison to the rays going through the other side of the beam which are not intercepted by the plate. The OPD in the three channels, r, g, and b in the reference paths in FIG. 3 of the block 110 which can be incorporated in FIG. 4 are adjusted 1 mm apart. For instance, the r channel is adjusted to have a reference path length longer by 1 mm than the green channel and the b channel to be shorter by 1 mm than the reference length of the g channel.

Three A-scans are obtained of the depth R distributed over the whole line of pixels, according to wavelength. They are then superposed in the PC reducing the speckle, according to the procedure described by N. Iftimia, B. E. Bouma, and G. J. Tearney, in Speckle reduction in optical coherence tomography by "path length encoded" angular compounding, J. Biomedical optics, 8(2), 260-263 (2003). The basic idea is that rays in the three channels enter the object under different angles and by angular average, speckle is reduced, similar to the procedure described at point 2 above using a C-scans.

Spectroscopic A-Scanning

In case the object has spectral properties, such as tissue, then it is important to provide spectroscopic OCT data. It is known that by measuring the reflectivity at different wavelength values, spectral absorption or spectral scattering can be assessed. Oximetry is one such field which can benefit. For oximetry for instance, the optical filter 19 has three peaks optimised on wavelengths to maximise the accuracy of oxygen concentration when using the three images delivered by the three colour parts of the sensor 3.

Black and white as well as colour cameras can be adapted, in which case a gray scale is obtained by known means of summing or weighting the contributions of the three spectral sensing parts.

Channeled Spectrum B-Scan Imaging

Two possible avenues of improving the embodiment in FIG. 4 are disclosed to produce B-scan OCT images.

Using a Transversal Scanner

A transversal scanner 85 can be added to scan the object beam over the target, using one or two mirrors, by means known in the art, such as galvo-scanners, resonant scanners, acousto-optic modulator or any other means which can scan the object beam angularly or laterally. Alternatively, a sliding mechanism, 91, can be used to laterally move the whole adapter and digital camera for manual scanning. For each lateral position achieved by actuating on the transversal scanner 84 or sliding mechanism 91, another A-scan is produced. By collecting several such A-scans for several presses of the shutter 9, and in this way a B-scan image can be assembled putting together the A-scans.

Light Line

Instead of projecting a spot to collect an A-scan from the depth at the spot location, a light line could be projected on the target and with cylindrical optics, better use of a 2D photo-sensor array is achieved, as presented by Endo, T., Yasuno, Y., Makita, S., Itoh, M. and Yatagai, T., in "Profilometry with line-field Fourier-domain interferometry," published in Opt. Express 13, 695-701 (2005). An additional cylindrical lens 66 is used to project a line illuminating image from either of the two sources, 4 or 6, on the sample 100, or this could be accomplished by converging optics 11 or 11' (which contains a spatial filter as well, 18, as detailed in FIGS. 1 and 2). In FIG. 4, the cylindrical lens 66 creates an illuminating line perpendicular to the figure plane. Some of the camera flashes are equipped with linear flash sources, in the form of linear filament bulbs or line capillaries filled with gas, others have their flash made from segments, in which case a linear segment can be advantageously used to generate a line. In this case, the cylindrical lens to condition the beam shape to a line is not necessary and a spatial filter 18 may be sufficient to spatially filter the flash light, in the form of a line slit. The light scattered back from the object 100 is transferred to the diffraction grating 42 where it is diffracted over the horizontal line of pixels in the photodetector array 3. If the camera has N lines and M columns of pixels, then for each pixel, (X,j) in the line projected on the object 100, for j=1 ... N, a spectrum is dispersed over the (1,j) to (M,j) pixels in the photodetector array line, j. The length of the line projected on the object 100 is returned to the columns of the photodetector array via lenses 41, 13, 62, 64 and 21 in the interface optics covering all columns, each column up to M meaning also three colour columns.

In the reference path in the block 110, another cylindrical lens is added, 67. The spatial filter 61 is a vertical slit in this case.

When using line illumination, the transversal scanner 85 has one mirror only to provide the repetition of B-scans for a different angular deflection of the beam. For each position, a new flash is shot and a new B-scan is acquired. For faster acquisition, the camera flash is replaced with an external faster flash unit. Alternatively, the IR beam emitted by 6 is continuously used. For even faster acquisition, an external more powerful optical source may be used in conjunction with the camera, 4".

Before any image acquisition, a screen 43 is introduced in the object beam to acquire images without the object. The images collected with the screen in, are deducted from images collected with the screen 43 removed. This eliminates or at least reduces the autocorrelation terms due to the reference beam.

Several images can be acquired in one flash burst, of the source 4 or 4" as well. In this case the flash is made longer and the camera is switched into movie regime.

Balance Detection Using Two Cameras

Figure 5:
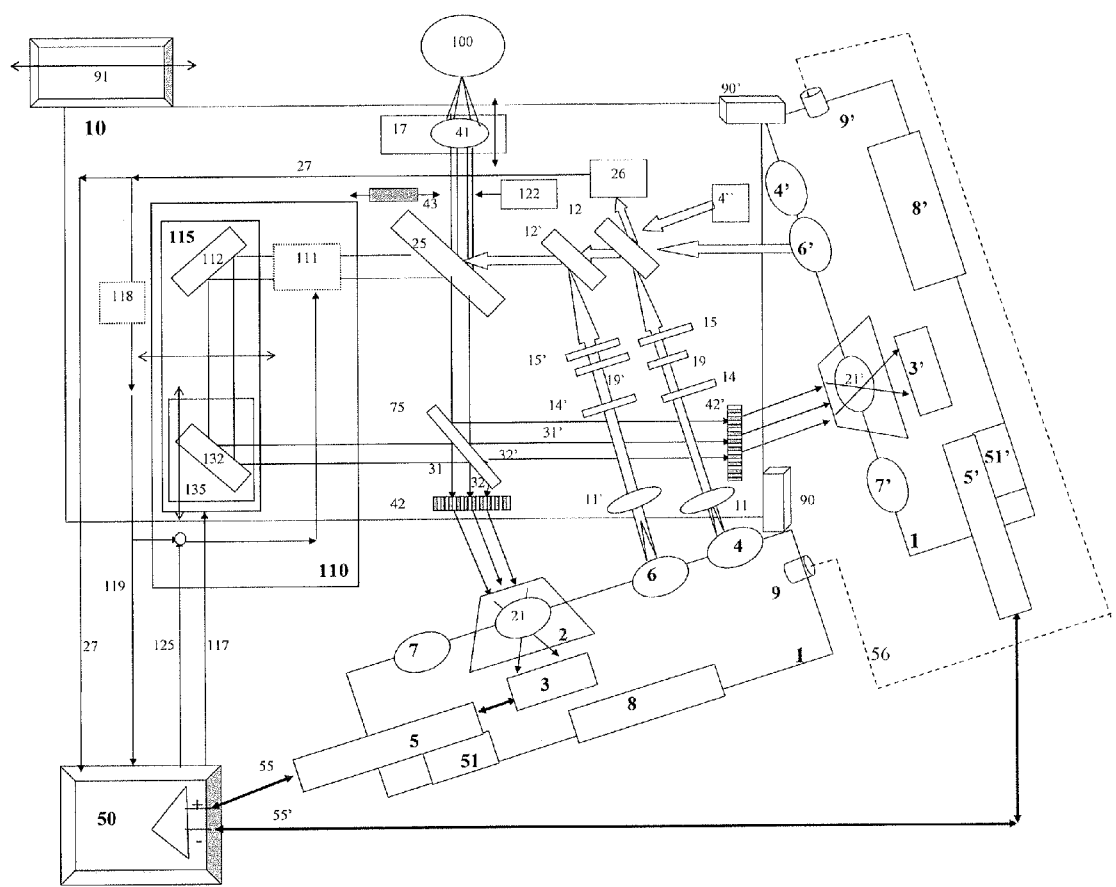
FIG. 5 shows a fourth embodiment of the present invention where two cameras are used in a balance detection CS-OCT set-up to obtain lower noise or mirror free cross section OCT images from the object.

Another embodiment of the present invention is presented in FIG. 5. Here two cameras, 1 and 1' are used, secured to the adapter in place via supports 90 and 90' and the reference beam transmitted via mirrors 112 and 132 on the stage 115, towards a second optical splitter, 75. Split reference beams 32, 32' and object beams 31 and 31' are sent to two conventional commercially available cameras 1 and V. The amount of overlap of object and reference beams on the gratings 42 and 42' is adjusted via a displacing means equipped with mirror 132 using a stage 135 and splitter 75. The signals from the two photodetector arrays, 3 and 3', are deducted and in this way, the noise around 0 Hz component is largely reduced, along with autocorrelation components within the reference beam and object beam. Two possibilities exist, either the two signals delivered by the photodetector arrays are subtracted, in case they are analogous and then the signal is digitized and an image is created by the PC 50. Simpler, the two images from the memory cards, 51 and 51', or the two digital images are directly fed via lines or remotely via 55 and 55' into the PC 50 and subtracted pixel by pixel. This is simpler but has the disadvantage of needing high dynamic range digital cameras. Both cameras are switched simultaneously using a mechanical device 56. Alternatively, if the cameras admit remote control, or external shutter facility, this will be used under a trigger control delivered by the PC 50.

In addition, light from both camera sources could be used to enhance the signal to noise ratio. Addition of IR beams from both sources 6 and 6' is shown in FIG. 5, although addition could be implemented for the flash beams emitted by sources, 4, as well.

The problem of mirror terms mentioned before in connection with the embodiment in FIG. 4 could here be addressed by altering the overlap of reference beams, 32 and 32' and object beams, 31 and 31', before reaching the diffraction grating 42 and 42', according to principles inspired from the theory pf Talbot bands as disclosed in the application WO2005040718 (A1) (GB2407155 (A) or EP1687586 (A0).

To adjust the OPD and compensate for dispersion, a method of spectral scanning delay line could be used as disclosed in WO2006024152 (A1).

Black and white as well as colour cameras can be adapted, in which case a gray scale is obtained by known means of summing or weighting the contributions of the three spectral sensing parts.

Simultaneous Reading of all Spectral Bands by the Same Set of Pixels

In previous embodiments, the colours from the smallest wavelength in the band b to the largest wavelength in the band r are dispersed along the sensor chip. In the example on using the camera for speckle reduction, if each A-scan covers 2 k pixels, then a 6 k line of pixels sensor is required. Each pixel however, outputs three signals depending on its colour filter. For the three groups of 2 k pixels, only one colour is used while the other two signals are discarded. Depending on the position of the pixel along the line of pixels within the dispersed line, the colour channel used and the two colour channels which are unused change. This is a waste of signal and time which can be improved using the embodiment in FIG. 6 where a multiplexer 140 superposes all the three bands on the same pixels. In this case, three A-scans can be collected with the same number of 2000 pixels in the example above, with advantage of speed and cost in the size of the sensor.

It is therefore advantageous to superpose the three bands along the same set of pixels in the camera. Let us say that for a given incidence direction to the diffraction grating, the diffracted angles of the rays in the centre of the three bands are $\phi_r$, $\phi_g$, and $\phi_b$. If the incident beams are adjusted with incidence varying according to these angles, then all three bands will be approximately superposed when diffracted within the same order of diffraction by the diffraction grating in reflection, 42 in FIG. 6. It should be obvious for those skilled in the art that equally, the diffraction grating can be used in transmission as well. To achieve the multiplexing, light out of the splitter 25 is diverted via mirror 141, towards the diffraction grating 42 after being reflected by a dichroic mirror, 142 which reflects one band and transmits the other two bands towards mirror 143, wherefrom light is directed towards dichroic mirror 144 which reflects a second band towards the grating 42 and the mirror 145 sends the third band towards the grating 42. By adjusting the distance between dichroic mirror 142 and mirror 141 and between dichroic mirror 144 and mirror 145, the incidence angles on the grating are conveniently adjusted in such a way, as all bands around a $\lambda_r$, $\lambda_g$, $\lambda_b$ are diffracted along a similar direction. A focusing element, a lens or a curved mirror 64 is used to convey the spread spectrum through the camera objective 21. Alternatively, if objective 2 could be removed, the focusing element 64 alone spreads the spectrum along the spectral direction over camera lines and the adapter is supplementary equipped with a covering lid, 150 to prevent any other light falling on the sensor 3. For instance, let us say that the optical source spectrum is 250 nm and three bands of 50 nm width each are spectrally selected about three peaks $\lambda_r$, $\lambda_g$, $\lambda_b$=675 nm, 575 nm and 475 nm, with three spectral gaps for better rejection of the other colours by each pixel, i.e. for lower cross-talk. It may be that each camera exhibits a different wavelength peak for the spectral windows r, g and b, the values above are for example only. Dark separating bands are also useful, because inside these spectral gaps, the transition of dichroic mirrors (filters) could be safely placed without distorting the associated correlation function on each channel which determines the depth selection. These dichroic mirrors are 112b and 112 g in the reference arm and 142 and 144 in the object arm. For this example, the dichroic mirror 142 could be a hot mirror with transition at 625 nm, while dichroic 144 is a hot mirror with transition at 525 nm. In this way, mirror 141 reflects the r peak of the spectrum with a maximum at 675 nm and the mirror 145 reflects the b peak of the spectrum with a peak at 475 nm.

The numerical values are for illustration only, the person skilled in the art should be able to adjust the filters correspondingly to fit any camera specs.

The multiplexer 140 could equally be used in the embodiment in FIG. 4 equipped with cylindrical optics to project a line over the object to be imaged. Equally, the multiplexer 140 can be used in a balance detection configuration of two cameras as disclosed in FIGS. 5 and 8. Possibly, two such multiplexers can also be employed, one for each diffraction grating 42, 42' and each camera, 1 and 1'.

Enhancing the Accuracy of Spectroscopic Channeled Spectrum OCT

The three paths in the reference arms in the embodiment in FIG. 6 are adjusted to be substantially equal. Three A-scans (or B-scans if cylindrical optics is used and a line is projected on the object) are produced by using the three spectral sensing parts r, g and b simultaneously. In this case, the narrow band filter 19 in front of the flash source 4 can be changed and acquisition repeated. For instance, 19 could be a filter with three narrow peaks, a peak in each of the band, r, g and b. Similar filters could be used in the r, g and b paths in FIG. 3. In one step acquisition, three A-scans are acquired for the set of filters. Then the filters are changed, where 19 has again three peaks, with a peak in each of the r, g and b bands but different from the previous case. For instance a long three peaks and a short three peaks filter 19 could be used, with the long filter with three peaks in the longer parts of the r, g and b bands while the short filter with three peaks in the shorter wavelength parts of the r, g and b bands. In this way, 6 A-scans can be acquired in two shots, 3 A-scans per each filter.

Another alternative is for filter 19 and filters 124r, 124g, 124b to be changed electrically under the line control 127r, 127g, 127b respectively. Liquid crystal filters are known which can electrically be tuned. In this way, spectroscopic depth analysis can be performed by collecting 6 A-scans for 6 different wavelengths in two shots only.

Simultaneous Acquisition of Microscopy Like and Cross Section OCT Images

Figure 7:
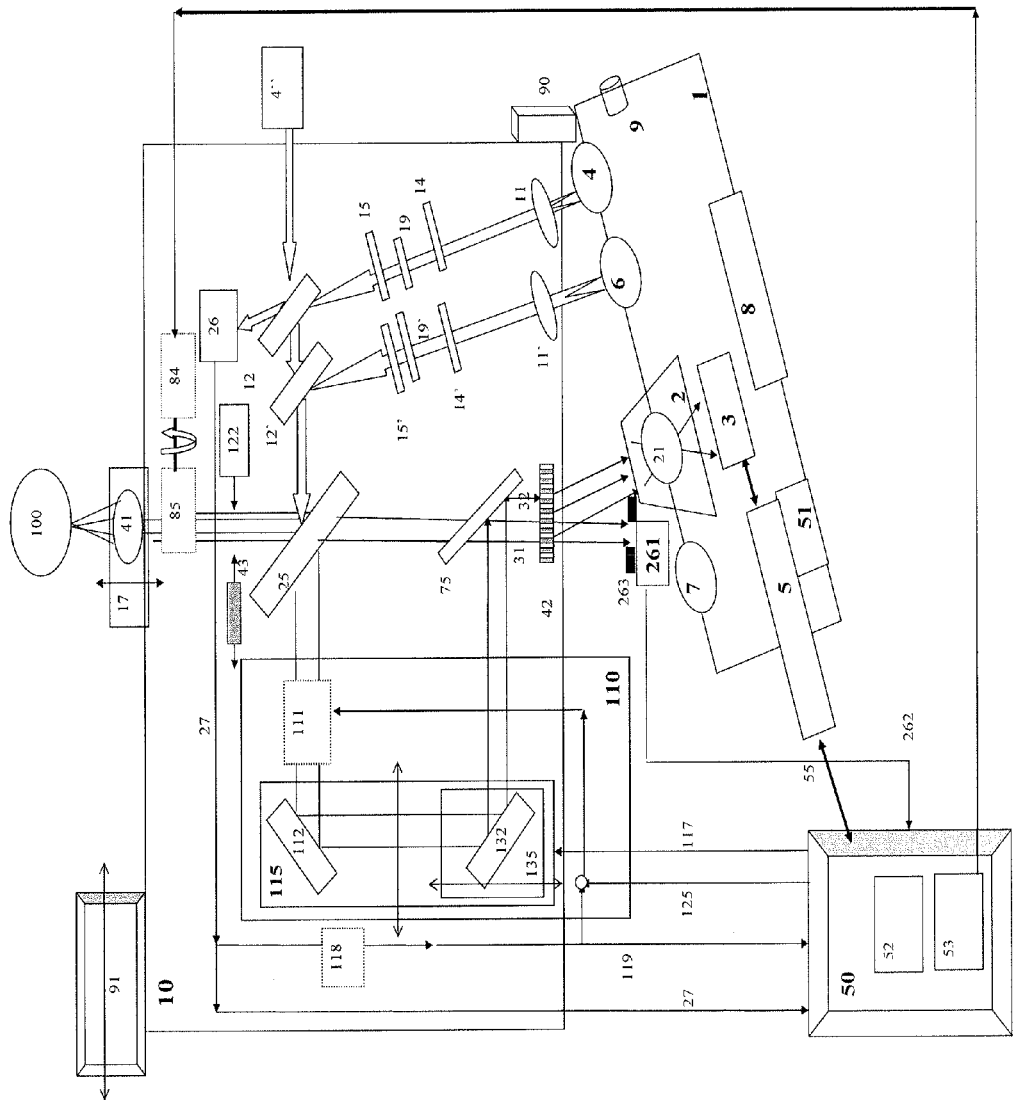
FIG. 7 shows a sixth embodiment of the present invention which provides simultaneously two measurements, low coherence interferometry and intensity or two images, an OCT image and a microscopy or SLO image.

An embodiment for simultaneous imaging in two channels is disclosed in FIG. 7. Here the translation stage 115 is used to shift the reference beam, 32, by reflection on the beamsplitter 75, just sufficiently laterally from the transmitted object beam, 31, in order to ensure that the aperture of the confocal receiver 261 intercepts the object beam only. In this embodiment, for reduced losses, the beamsplitter 75 has a low reflectivity and high transmission. To restrict the aperture of the confocal receiver 261, optical fibre, a pinhole or a slit in front of the receiver 261 can be used, this also enhance the confocality. In the embodiments in FIGS. 4-6, simultaneous imaging in two channels is not possible as the object and reference beams are superposed. Sequential imaging in these embodiments becomes possible by blocking the reference beam. However, it is important to have an en-face image to guide the investigation in the OCT regime. This would require diverting some of the object beam towards a photodetector or a different camera. This would reduce the intensity of interference. Therefore, the embodiment in FIG. 7 makes use of the zero order of diffraction which is not used in the CS-OCT regime and is discarded in the embodiments in FIGS. 4-6. Alternatively, when the dispersing element in the spectrometer is using a prism instead of the diffraction grating 42, the embodiment makes use of the light reflected from one of the prism facet. To use this signal, first the reference beam is shifted laterally. It is now obvious that the reason for the lateral relative shift of the two beams in the embodiment in FIG. 5 is different than that in FIG. 7. In FIG. 5, the goal was to eliminate the mirror terms. In FIG. 7, the goal is to shift the beams laterally just sufficient to eliminate the reference beam from the aperture of the confocal receiver 261. In the embodiment in FIG. 7, mirror terms will still exist, but reduced proportional to the amount of lateral shift of the two beams, object and reference.

The signal from the confocal receiver 261 is applied along line 262 to the measuring block, 52, in the PC 50. In case a galvoscanner is added, 85, the measuring block 52 operates as a frame grabber to generate the fundus or SLO image or microscopy image. The galvoscanner is controlled by block 53 in the PC50.

Two Regimes of Operation are Possible

Flying Spot

In this case, the output beam is focused to a point in the object. The adapter with the camera is used for simultaneous measurements of intensity provided by the receiver 261 and a reflectivity profile in depth, A-scan is generated using the sensor 3, read as a line camera.

For imaging, an XY-scanner head 85 is added which is equipped with two mirrors and the beam is scanned in a raster fashion using the driver 84. The confocal receiver 261 is in this case a point photodetector. Simultaneous OCT volume acquisition using the sensor 3 and en-face SLO (microscopy) imaging using photodetector 261 is achieved by using the transverse scanner 85. Here the sensor 3 is used to generate A-scans and the volume is assembled from such A-scans or from B-scans formed by grouping several A-scans.

Flying Line

In this case, a line is generated using cylindrical optics to project the source beam in the shape of a line on the object, or by using a line shaped optical source, such as a line filament bulb or a discharge gas source with the gas confined to a cylindrical shape. Simultaneous measurement is possible where the line camera 261 provides an integrated T-scan from the object over the depths within the confocal profile and the sensor 3 provides a B-scan OCT image. Conventional 2D cameras customised as line cameras can be used as well as linear CCD or CMOS cameras, analog or digital. To restrict the aperture of the confocal receiver, a slit can be used in front of the line camera 261. For volume imaging, a scanner head 85 is added which has one galvo-mirror only and the driver unit 84 requires one generator only. The sensor 3 is used to deliver a B-scan OCT image for each position of the galvomirror 85.

Simultaneous OCT volume acquisition using the sensor 3 and en-face SLO (microscopy) imaging using the line camera 261 is achieved by using the transverse scanner 85. Here the sensor 3 is used to generate B-scans and the volume is assembled from such B-scans while the T-scans generated by the line camera 261 are grouped together within an en-face image (microscopy, SLO or fundus image).

Let us say that the camera 1 operates at 100 microsecond acquisition time. Then, a flash source emitting for slightly longer than 10 ms or a continuous source 4" can be used to acquire several shots, let us say 100, and in doing so, the galvo 85 moves the line projected on the sample to a new line position out of 100 possibilities within the raster to be finally produced. The frame grabber 52 now collects line data for each new line position and generates an en-face SLO or microscopy image from 100 such T-scans. The en-face image is completed and displayed by the frame grabber 52 in the PC 50, while the volume is acquired by the OCT channel. 100 B-scan OCT cross sections are ready for subsequent inspection. The en-face image so generated can advantageously guide the acquisition of volumes as well as its subsequent visualisation of differently oriented sections in the object. This image is not inferred like in prior art from B-scans, but generated live using signal in the zeroth order of diffraction (when using a diffraction grating) or reflected by the prism in the spectrometer set-up when using a prism.

Figure 8:
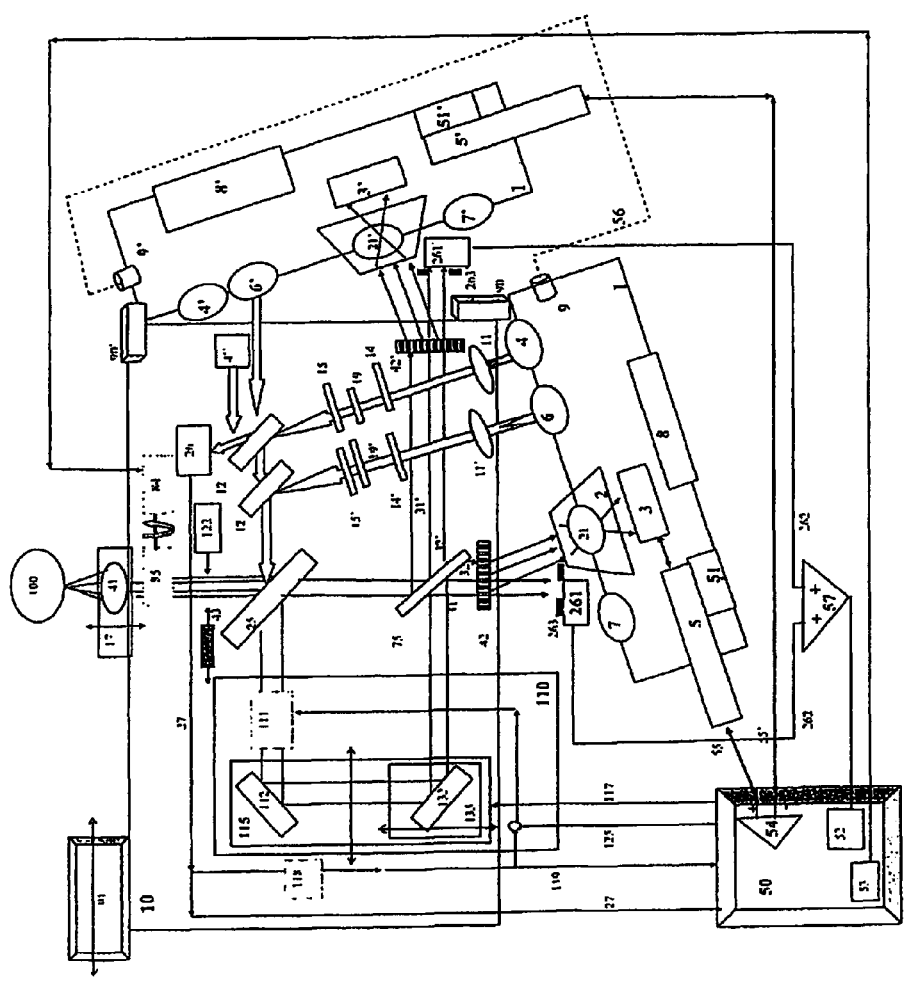
FIG. 8 discloses a seventh embodiment of the present invention which provides a more efficient and less noisy equivalent of the embodiment in FIG. 7.

The embodiment in FIG. 8 represents an efficient set-up, where all signals out of the beamsplitter 75, now 50/50, are used. A balanced configuration with two cameras, 1 and 1' for balanced OCT and two photodetectors, 261 and 261' are used to intercept the zero order of diffraction. Here the translation stage 115 is used to shift the reference beam just sufficiently laterally in order to ensure that photodetector 261 and 261' intercept the object beams only. Pinhole 263, 263', slits or fibre optics are used to restrict the aperture of the photodetectors 261 and 261'. The signals delivered by the two cameras are deducted in the differential amplifier 54. The signals delivered by the two confocal receivers 261 and 261' are summed up in the summator 57.

Alternatively, for the embodiments in FIG. 4-6 where line shaped beams are used to illuminate the object, separate line optical sources can be employed for better performance. Such a source could be a stripe shaped SLD, a filament bulb or a linear discharge gas lamp with better stability of the discharge than the lamps used in cameras.

Figure 9:
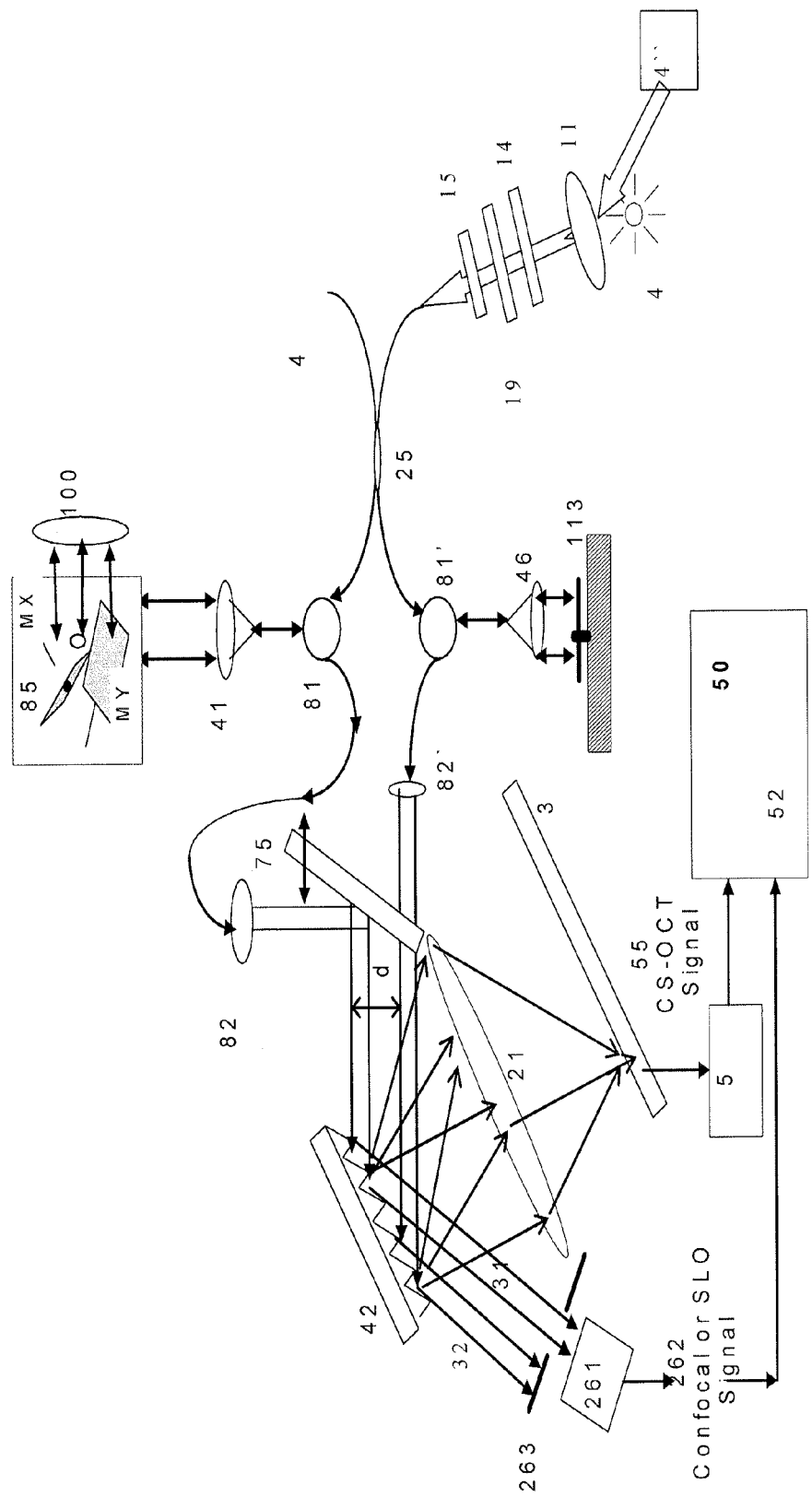
FIG. 9 describes an embodiment where the main splitter is in fibre and light from the optical source is confined to fibre.

The embodiment in FIG. 7 is implemented with division of light using optical fibre as disclosed n FIG. 9. Light from the optical source is confined to the directional coupler 25, replacing the main bulk splitter in previous embodiments. Light is divided into two arms, object, along the circulator 81 and reference arm, circulator 81'. Light at the fibre outputs is collimated using focusing elements 82 and 82'. The collimated beams via transmission through splitter 75 and respectively reflection, reach the diffraction grating 42. The splitter 75 has a high reflectivity and low transmission. To adjust the gap, d, between the two beams, object 31 and shifted reference, 32, displacing means are used, equipped with the splitter 132 which can be moved using the translation stage 135 and a splitter 75 which can also be moved horizontally. The spectrometer set-up consists in the dispersing element 42, focusing element 21 and sensor 3. A pinhole 263 is used to obscure the zero order of the diffracted reference beam, 32.

It should be obvious for those skilled in the art to customise the zero order diffraction order signal in the embodiments in FIGS. 7, 8 and 9 into providing the SLO as well as a fluorescence signal, as all wavelengths are angularly diffracted along the same direction in the zero$^{th}$ order. Suitable spectral filters could be used in conjunction with other confocal receivers (in the form of point photodetectors or line cameras) to provide confocal and fluorescence signals simultaneously.

It should be also obvious that were a diffraction grating was used as a dispersing element, a prism could equally be used and the other way around. If the dispersing element was a prism, then reflections from the prisms can be used to generate the simultaneous measuring signal in the confocal receiver, and the prism can be supplementary coated with a reflective layer to enhance this reflection. If the dispersing element was a diffraction grating, then the zero order of diffraction is used to generate the confocal signal, in this case preferably the effort is in concentrating the power towards the diffraction order used, by procedures known by the diffraction grating manufacturers, such as blazing. Obviously, in the embodiments presented where a diffraction grating is used in transmission, it could equally be used in reflection and in the embodiments presented where a diffraction grating is used in reflection, could equally be used in reflection.

Further Details

The further details set out below may be provided in the adapter alone or in combination.

The camera adapter based optical imaging apparatus may be equipped with a first dispersing element to provide spectral analysis of the light output from the said interferometer along one directions of pixels in the said photodetector sensor representing a spectral direction and by evaluating the Fourier transformation of the signal collected along the spectral direction covering the spectrum of the said optical source, producing a depth reflectivity profile of the object.

The dispersion element may be a prism.

Alternatively, the dispersion element may be a diffraction grating.

The camera adapter may be equipped additionally with a second dispersing element separated by a focusing element from the said first dispersion element to linearise the signal output of the photodetector sensor along the spectral axis versus the wave-number $2\pi/\lambda$ with $\lambda$ the wavelength of the said optical source.

The sensor array in the digital camera may be a colour array and delivers signals from each pixel corresponding to spectral components in three bands, r, g, b, centred on respectively $\lambda_r$, $\lambda_g$, $\lambda_b$ wavelength values as part of the spectrum of the said optical source which when downloaded from the pixel lines along the spectral axis of the said photodetector array produces via Fourier transformation an r-A-scan, a g-A-scan and a b-A-scan and light from the interferometer is spectrally split in angle using spectral splitters and mirrors in such a way as the three optical bands, r, g, b fall at different incidence angle on the 1$^{st}$ dispersion element in such a way that all bands are dispersed along substantially the same direction along the said photodetector sensor. In order to use the same set of pixels for photodetecting all three bands simultaneously, the optical delay block operates spectral selection in the three separate paths, r, g, b along three r, g, b arms tuned on the three spectral different bands, the optical delay block returning three optical r, g, b waves to the said beamsplitter, where each wave encounters a different path length independently adjusted in relation to the other two.

The three path lengths, r, g, b in the optical delay block may be adjusted to be substantially the same and the said photosensor array outputs three A-scans, one for each colour r, g, b and where the three A-scans, r-A-scan, g-A-scan and b-A-scan provide depth resolved spectroscopic information about the object at one press of the shutter button.

The adapter may additionally use a microscope slide providing an optical delay d for the rays going through it in comparison with the rays through air which is introduced halfway through into the object beam and the spectral paths r, g, b in the optical delay block are adjusted in steps of d to substantially superpose in depth the r A-scan, the g A-scan and the b A-scan to reduce the speckle within a compound resulting A-scan at one press of the shutter button.

The flash optical interface may prepare a polarisation state for the optical source light and the three reference paths lengths, r, g, b in the reference block are adjusted to be substantially the same and where each spectral reference path r, g, b is provided with a polarisation element imprinting a different polarisation characteristic to each reference wave returned to the beamsplitter and where the said polarisation element is chosen from the category of linear polarisers or waveplates and the said photodetector outputs three A-scans, one for each colour r, g, b and where the three A-scans provide depth resolved polarisation information about the object at one press of the shutter button.

The optical source interface may project a line over the object using cylindrical symmetry optics and at least one focusing element before the digital camera has cylindrical symmetry where the image captured by the said photodetector array is a B-scan image formed from A-scans along the spectral decomposition axis and lateral extension along the direction of the line projected by the optical source interface over the object.

The focusing element with cylindrical symmetry may be a cylindrical lens.

The focusing element with cylindrical symmetry may be a cylindrical mirror.

In case the camera flash has cylindrical symmetry, then linear spatial filters are used in the optical source interface.

The low coherence interferometer contains two beamsplitters to route the object and reference beams to implement balance detection and convey substantially equal strength object beams and equal strength reference beams to two similar digital cameras and where the images from the two images are subtracted.

The $1^{st}$ beam-splitter divides the light from the said optical source into an object beam conveyed to the said object and a reference beam towards an optical delay block and where light from the object is returned via the adapter and the $1^{st}$ beamsplitter to a $2^{nd}$ beamsplitter and where the optical delay block works in transmission sending the reference beam towards the $2^{nd}$ beamsplitter and where the second beamsplitter has a ratio of 50/50.

Simultaneous measurements and dual channel simultaneous imaging based on spectral interferometry and confocal detection are made possible by employing the stray signals when performing spectral decomposition. When spectral decomposition is achieved via diffraction using a diffraction grating in transmission or in reflection, the stray zero diffraction order is employed by a confocal receiver. When spectral decomposition is achieved via dispersion using a prism, then reflections from the prism facets are used in the confocal receiver. These stray signals are proportional to the intensity of the object beam incident on the diffraction grating or on the prism used by the spectral decomposition component. To avoid saturation of the confocal receiver due to the strong signal in the reference arm, the reference beam is laterally shifted before spectral decomposition away from the confocal aperture.

Simultaneous measurement and imaging in two channels OCT and confocal (SLO) can operate with one or two cameras in a balance detection configuration for the OCT channel and by summing the two stray signals for the confocal detection.

4. SUMMARY OF METHODS

A method of high resolution depth resolved measurement of an object which employs an adapter which transforms a commercially available digital camera into a depth resolved measurement instrument, by making use of the elements equipping the commercially available digital camera to illuminate the object observed as well as ensure that light from the object is transferred to the said commercially available camera, and where the said commercially available camera is equipped with at least an optical source, a photodetector array and a shutter button.

The method may use the said optical source associated to the camera as a low coherent source to drive a low coherence interferometer implemented in the adapter.

The method may use phase shifting interferometry to produce at least three interference images for three phase shifts and where an enface OCT image from the object is assembled from the at least three steps and where each step for phase shifting and the switch on of light from the said optical source are controlled by pressing the shutter button.

The method may use a digital colour camera with m sets of pixels with each set sensitive to a given colour band to generate simultaneous m OCT information sets using each set of pixels as part of a distinct OCT channel.

The method may use a two arms low coherence interferometer and where the optical path difference between the lengths of the two arms can be adjusted independently for each of the m colour bands.

The method may use a phase shifting interferometry method to recover OCT information implemented in one step using the m sets of pixels in the photodetector array.

In the method there may be m=3 spectral bands, r, g and b of central wavelengths $\lambda_r, \lambda_g, \lambda_b$, and signals delivered by each colour channel in the camera are used to sense the OPD corresponding to that respective spectral band and where the three OPD values are adjusted as 0 $\lambda_i$, $\lambda_j/3$ and $2\lambda_s/3$ where i, j and s could be any set of permutations of r,g,b and where three interference images are generated by the said colour sensor array, one for each band r, g, b, with $I_r$, $I_g$, and $I_b$, the intensity of the photodetected signal provided by each colour pixel and where a C-scan OCT image is assembled for each pixel in the C-scan image using the values of the same pixel in the three interference r, g, b images evaluated as: $s=\sqrt{(I_r-I_g)^2+(I_g-I_b)^2+(I_r-I_b)^2}$, where such OCT image is generated after pressing the said shutter button once.

In the method with m=3 spectral bands, r, g and b have central wavelengths $\lambda_r, \lambda_g, \lambda_b$, and where the signals delivered by each colour channel in the camera are used to sense the OPD corresponding to that respective spectral band and where at the first press of the said shutter button an optical path difference between each reference path length and the object path length is set at zero, the three channels collecting intensities $I_{1p}$, with p=r,g,b, where at the second press of the shutter button the OPD values are set at $\lambda_r/3$ in the r reference path, $\lambda_g/3$ in the g reference path and of $\lambda_b/3$ in the b reference path and intensities $I_{2p}$, with p=r,g,b are acquired and where at the third press of the shutter button OPD values are set at $2\lambda_r/3$ in the r reference path, $2\lambda_g/3$ in the g reference path and at $2\lambda_b/3$ in the b reference path and intensities $I_{3p}$ are acquired, with p=r,g,b, and where three C-scan OCT image of $s_p=\sqrt{(I_{1p}-I_{2p})^2+(I_{1p}-I_{3p})^2+(I_{2p}-I_{3p})^2}$ on each pixel with p=r, g, b are assembled for each colour r, g, b in the said sensor from the three interference images acquired for the three presses of the shutter button.

The adapter may implement spectral decomposition of the light output from the said low coherence interferometer and where the spectrum dispersed by spectral decomposition is read by the photo detector array in the said digital camera to produce by its Fourier transformation, a reflectivity profile in depth through the said object at the press of the shutter of the said digital camera.

The method may use m reflectivity profiles generated by each set of colour pixels.

The method may use the output of the said low coherence interferometer spectrally separated in the said m bands which are angularly diverted at different angles of incidence before being subject to spectral decomposition, where the angles are adjusted in such a way that the rays of central wavelength of all three bands after spectral decomposition are angularly dispersed along a substantial similar direction to cover the same set of pixels in the said photodetector array to be used to deliver the m OCT reflectivity profiles.

Light from a low coherent source may be conditioned to project a light line on the object along an object lateral direction and N pixels in the 1st direction of the said photodetector array in the digital camera are used to sense the lateral distribution of object reflectivity along the object lateral direction while M pixels along the 2nd direction of the photodetector array in the digital camera are used for the said operation of spectral decomposition to produce the said reflectivity profile for each pixel up to N in the line along the $1^{st}$ direction to generate m B-scan images of N by M pixels which map object lateral direction by depth respectively.

The said low coherent source may be the flash source of the same digital colour camera, or the IR beam, or any external flash or pulse source where the flash time length can be independently adjusted from the integration time of the sensor 3 (3') in the camera 1 (1'). Alternatively, the adapter may make use of a CW optical source when many frames are acquired.

An alternative method of high resolution imaging of an object based on a two beams low coherence interferometer, under illumination from a low coherent source, of an object beam being sent to the object through the interferometer to collect reflectivity of the object and the other a reference beam, and where the interferometer has means to adjust the optical path difference of the path lengths utilised by the object and reference beams and is terminated on a 50/50 splitter which outputs a $1^{st}$ object beam and a $1^{st}$ reference beam, a $2^{nd}$ object beam and a $2^{nd}$ reference beam and where the interference signals from the $1^{st}$ object and $1^{st}$ reference beams is in anti-phase with the interference signal from the $2^{nd}$ object and the $2^{nd}$ reference beam and where the set of $1^{st}$ object and $1^{st}$ reference beams suffer spectral decomposition which is analysed by a $1^{st}$ digital camera and the set of the $2^{nd}$ object and $2^{nd}$ reference beams suffer spectral decomposition which is analysed by a $2^{nd}$ digital camera and where the camera signals are deducted in a balance detection configuration to enhance the signal corresponding to the modulation of the spectral decomposition and where the amount of overlap of the $1^{st}$ object beam and $1^{st}$ reference beam and of the $2^{nd}$ object beam and $2^{nd}$ reference beam is adjustable before spectral decomposition to produce higher strength of modulation of the spectral decomposition for one sign of the optical path difference than for the other sign of the optical path difference in the interferometer.

In addition, confocal signals microscopy can be implemented as described above, by using the stray signals associated with diffraction or dispersion, to enable a dual simultaneous measurement or imaging technique, to produce combined signals OCT/CM for microscopy or OCT/SLO when imaging the retina. In this case, the method is to balance the spectral interferometry signals and sum the confocal stray signals. The stray signals represent signals proportional to the intensity of the object incident beam to the dispersion component.

The low coherent source may be a flash source associated to one or both of the said digital cameras.

5. CONCLUDING REMARKS

It should be obvious for those skilled in the art that other implementations are possible. For instance, light from the flash lamps 4 and from IR beam source 6 in the embodiments in FIGS. 1, 2, 4 and 6 could be sent directly to the object 100 and not via optical splitters, such as 25.

Similarly, it should be obvious for those skilled in the art that light from the flash lamps 4, 4' and from IR beams 6 and 6' in embodiments using two cameras, such as that disclosed in FIG. 5, could be sent directly to the object 100 and not via optical splitters, such as 25.

It should be obvious for those skilled in the art that steps in the OPD could equally be introduced in the object path to achieve the same functionality as that presented here applying changes to the reference path only.

It should also be obvious for those skilled in the art that the novel methods disclosed here are applicable if a separate optical source is used, not in the same case (box) as that containing the sensor. High performance low cost detached photographic flashes, TTL controlled exist and they could be employed similarly according to the disclosure. Also, it should be obvious for those skilled in the art that the novel methods disclosed here are applicable in cases using professional black and white cameras or professional colour cameras, or cameras which have more than c=3 colour sensors cameras.

It should also be obvious that to avoid reflections from different constitutive elements, some may be eliminated from the embodiments presented without departing from the scope of the invention. Also, where lenses or microscope objectives were mentioned, they could be replaced by reflective converging elements, such as spherical or parabolic mirrors.

The invention claimed is:

1. A camera adapter, for transforming a camera device having a housing containing a camera into an imaging instrument of an object, where the camera in the camera device has at least an optical illumination source creating excitation light, a photodetector array sensor behind an entry, a shutter release and a memory,
   wherein the camera adapter is adapted to be placed between the camera device and the object and comprises:
   a housing removable frame having securing fittings to hold the camera device 10 securely in place,
   which housing removable frame comprises: a first light output to transfer light to the object,
   a second light output placed on the adapter in front of the commercial camera housing device for directing light from the adapter onto the photodetector array, at least a light input for accepting excitation light from the at least an optical illumination source of the commercial camera housing device,
   means for directing the excitation light from the at least one light input towards the first light output, where the means for directing excitation light employ at least an element out of the group of deflecting mirrors and beamsplitters,
   an object interface for directing light from the object into the second light output,
   so that the camera device is employed to collect an image of the object via the adapter into the memory of the camera device.

2. Camera adapter according to claim 1, where the object interface is equipped with at least an element out of the group of deflecting mirrors, beamsplitters and focusing elements out of the group of lenses and curved mirrors.

3. Camera adapter according to claim 1, where the means for directing excitation light deploy light off-axis to the light output.

4. Camera adapter according to claim 1, where the means for directing excitation light are equipped with at least one element of the group of: pinholes, wavelength filters, polarisers, waveplates, attenuators, converging and diverging elements to adapt the divergence of the beam of light delivered by the at least an optical illumination source to the size of the object illuminated area.

5. Camera adapter according to claim 4, where when the means for directing excitation light contains at least an element of the group of waveplate and polariser, the interface optics contains a polarisation rejection analyser equipped with at least one of the following: waveplate and polariser to reduce stray reflections obscuring the object examined.

6. Camera adapter according to claim 1, where the object is the retina of a human or animal eye and where the adapter transforms the camera device into a fundus imaging system, and where the focusing means, together with the focusing of the eye anterior chamber of the eye, form an image of the retina on the photodetector array of the commercial camera housing device.

7. Camera adapter according to claim 1, where the camera device is equipped with two optical illumination sources, an infrared light to guide camera autofocus and a visible light for flooding the object in the process of image taking,
  a camera focusing element placed at the entry,
  autofocus means and
  a display screen for the image collected
    where the adapter has two light inputs, one for each illumination source and where the means for directing excitation light, superpose the light from both light inputs into the same beam directed towards the first light output.

8. Camera adapter according to claim 7, where the adapter transforms the camera device into a fundus imaging system, where the focusing means together with the camera focusing element and together with the focusing of the eye anterior chamber of the eye, form an image of the retina on the photodetector array of the commercial camera housing device.

9. Camera adapter according to claim 1, equipped with an auxiliary illumination source directing light towards the means for directing the excitation light.

10. Camera adapter according to claim 1, where the photodetector array of the camera device is a colour sensor with three colour sensitivities in spectral windows r, g, b and where
  the means for directing excitation light supplementary contains one to three optical filters centred on the maximum of sensitivity within the spectral windows r, g, b.

11. Camera adapter according to claim 1 which supplementary contains interchangeable filters placed in the path of the excitation light,
  a synchronous device, which is triggered by the emission of light by the commercial camera housing device that acts upon sequential change of optical filters.

12. Camera adapter according to claim 11 where the synchronous device is
  toggled by the shutter of the commercial camera housing device to change a filter at a time, or when the camera is equipped with a repetitive collection function of images, to change several filters in sequence.

13. Method of investigation of an object, which uses a camera device and an adapter, where
  the camera device having a housing containing a camera, where the camera in the camera device has at least an optical illumination source creating excitation light, a photodetector array sensor behind an entry, a shutter release and a memory
  the adapter comprises:
  a housing removable frame having securing fittings to hold the camera device, securely in place,
  which housing comprises
  a first light output to transfer light to the object,
  a second light output for directing light from the adapter onto the photodetector array,
  at least a light input for accepting excitation light from the at least an optical illumination source of the commercial camera housing device,
  means for directing the excitation light from the at least one light input towards the first light output,
  an object interface for directing light from the object into the second light output,
  the method comprising positioning the camera device inside the adapter in such a way as:
  (i) the light input of the adapter collects excitation light from the at least one illumination source of the camera and (ii) the second light output fits the entry to the camera,
  wherein the method comprising operating the camera part of the camera device together with the adapter to:
  (i) spatially adjust the location of the camera device and adapter in front of the object by monitoring the camera display; and
  (ii) perform focusing on the object through the adapter and
  (iii) acquire an image of the object on the memory of the camera by pressing the shutter of the commercial camera housing device;
  where excitation light is added from an optical source attached or placed inside the adapter.

14. Method of investigation of an object according to claim 13, where when the camera is equipped with a camera focusing element at the entry, the method comprising operating the camera part of the camera device together with the adapter to supplementary perform focusing on the object through the adapter using the autofocus of the camera.

15. Method of investigation of an object according to claim 13, where the adapter is equipped with optical filters for the excitation light, which are changed via a synchronous circuit under the control of the excitation light and where for each press of the shutter of the camera, a filter is changed inside the adapter when light from the excitation light is detected by the synchronous circuit and the images so collected for each filter are downloaded from the memory into a computer or sent wirelessly to a computer where they are combined to perform spectroscopic analysis of the object.

16. Method of investigation of an object, which uses a camera device and an adapter, where
  the camera device having a housing containing a camera, where the camera in the camera device has at least an optical illumination source creating excitation light, a photodetector array sensor behind an entry, a shutter release and a memory
  the adapter comprises:
  a housing removable frame having securing fittings to hold the camera device, securely in place,
  which housing comprises
  a first light output to transfer light to the object,
  a second light output for directing light from the adapter onto the photodetector array,
  at least a light input for accepting excitation light from the at least an optical illumination source of the commercial camera housing device,
  means for directing the excitation light from the at least one light input towards the first light output,
  an object interface for directing light from the object into the second light output,
  the method comprising positioning the camera device inside the adapter in such a way as:
  (i) the light input of the adapter collects excitation light from the at least one illumination source of the camera and (ii) the second light output fits the entry to the camera,
  wherein the method comprising operating the camera part of the camera device together with the adapter to:

(i) spatially adjust the location of the camera device and adapter in front of the object by monitoring the camera display; and
(ii) perform focusing on the object through the adapter and
(iii) acquire an image of the object on the memory of the camera by pressing the shutter of the commercial camera housing device;

where the adapter is equipped with optical filters for the excitation light, which are changed via a synchronous circuit under the control of the excitation light and where for each press of the shutter of the camera, a filter is changed inside the adapter when light from the excitation light is detected by the synchronous circuit and the images so collected for each filter are downloaded from the memory into a computer or sent wirelessly to a computer where they are combined to perform spectroscopic analysis of the object.

17. Method of investigation of an object according to claim 16, where when the camera is equipped with a display screen, adjustment of internal elements in the adapter such as focusing means and means for directing excitation light are guided by the display screen of the camera in order to achieve maximum brightness, maximum sharpness and minimisation of stray reflections in the image.

* * * * *